(12) United States Patent
Kang et al.

(10) Patent No.: US 8,003,093 B2
(45) Date of Patent: *Aug. 23, 2011

(54) B CELL-BASED VACCINE LOADED WITH THE LIGAND OF NATURAL KILLER T CELL AND ANTIGEN

(75) Inventors: Chang-Yuil Kang, Seoul (KR);
Yeonseok Chung, Seoul (KR);
Hyun-Jeong Ko, Seoul (KR);
Yeon-Jeong Kim, Changwon-si (KR);
Byung-Seok Kim, Suwon-si (KR);
Sung-Youl Ko, Bucheon-si (KR)

(73) Assignee: Seoul National University Industry Foundation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 11/718,391

(22) PCT Filed: Apr. 27, 2006

(86) PCT No.: PCT/KR2006/001589
§ 371 (c)(1),
(2), (4) Date: Oct. 2, 2007

(87) PCT Pub. No.: WO2007/126163
PCT Pub. Date: Nov. 8, 2007

(65) Prior Publication Data
US 2010/0028380 A1    Feb. 4, 2010

(51) Int. Cl.
*A01N 63/02* (2006.01)
*A61K 39/00* (2006.01)
*A61K 39/02* (2006.01)
*A61K 39/12* (2006.01)

(52) U.S. Cl. .............. 424/93.71; 424/184.1; 424/204; 424/234

(58) Field of Classification Search .................. None
See application file for complete search history.

(56) References Cited

U.S. PATENT DOCUMENTS
2006/0216316 A1* 9/2006 Dhodapkar et al. ....... 424/277.1

OTHER PUBLICATIONS

Abstract of Wheeler (Salud p'ublica de M'exico, (Jul.-Aug. 1997) 39 (4) 283-7).*
Efferson et al (Anticancer research, 2005, vol. 25, pp. 715-24.*
Bachman et al (Journal of Immunology, 2005, vol. 175, pp. 4677-4685.*
Abstract of Kim et al (Journal of Immunology, Apr. 1, 2006, vol. 176, suppl S, p. S260).*
Abstract of Ko et al (Journal of Immunology, Apr. 1, 2006, vol. 176, suppl S, p. S260).*
Fujii et al (Journal of Immunological Methods, 2003, vol. 272, pp. 147-159).*
Singh et al (Journal of Immunology, 1999, vol. 163, pp. 2373-2377).*
Chang et al (Journal of Experimental Medicine, May 2005, vol. 201, pp. 1503-1517).*
Lang et al (Immunology, 2004, vol. 112, pp. 386-396).*
Brandsma et al (Journal. of Virology, 2004, vol. 78, pp. 116-123).*
Wang et al (Journal of Immunology, 2004, vol. 173, pp. 6357-6365).*
Hans, J.J. et al., "Potent expansion of human nautral killer T cells using α-galactosylceramide (KRN7000)-loaded monocyte-derived dendritic cells, cultured in the presence of IL-7 and IL-15," J. Immun. Methods., 247, 61-72, (2001).
Zeytin He, et al., "Combination of a Poxvirus-Based Vaccine with a Cyclooxygenase-2 Inhibitor (Celecoxib) Elicits Antitumor immunity and Long-Term Survival in CEA.Tg/MIN Mice," Cancer Res., 64(10):3668-3678, (2004).
Reilly RT, et al., "The Collboration of Both Humoral and Cellular HER-2/neu-targeted Immune Responses is Required for the Complete Eradication of HER-2/neu-expressing Tumors," Cancer Res., 61(3):880-883, (2001).

* cited by examiner

*Primary Examiner* — Karen Canella
(74) *Attorney, Agent, or Firm* — Joseph Hyosuk Kim; JHK Law

(57) ABSTRACT

The present invention relates to a B cell-based vaccine loaded with the ligand of natural killer T cell and antigen for the prevention and treatment of disease, more precisely, an immunotherapeutic and prophylactic vaccine mediated by B cells loaded with α-galactosylceramide, a kind of glycolipid which can stimulate natural killer T cells. A vaccine composition of the present invention can be effectively used as an antitumor immunotherapeutic agent. B cells therein, which are easily obtainable compared with dendritic cells, not only induce a similar level of cytotoxic T lymphocyte response to that of the conventional dendritic cell-based vaccine but also have a prophylactic and therapeutic effect on solid tumor and metastatic tumor.

12 Claims, 30 Drawing Sheets

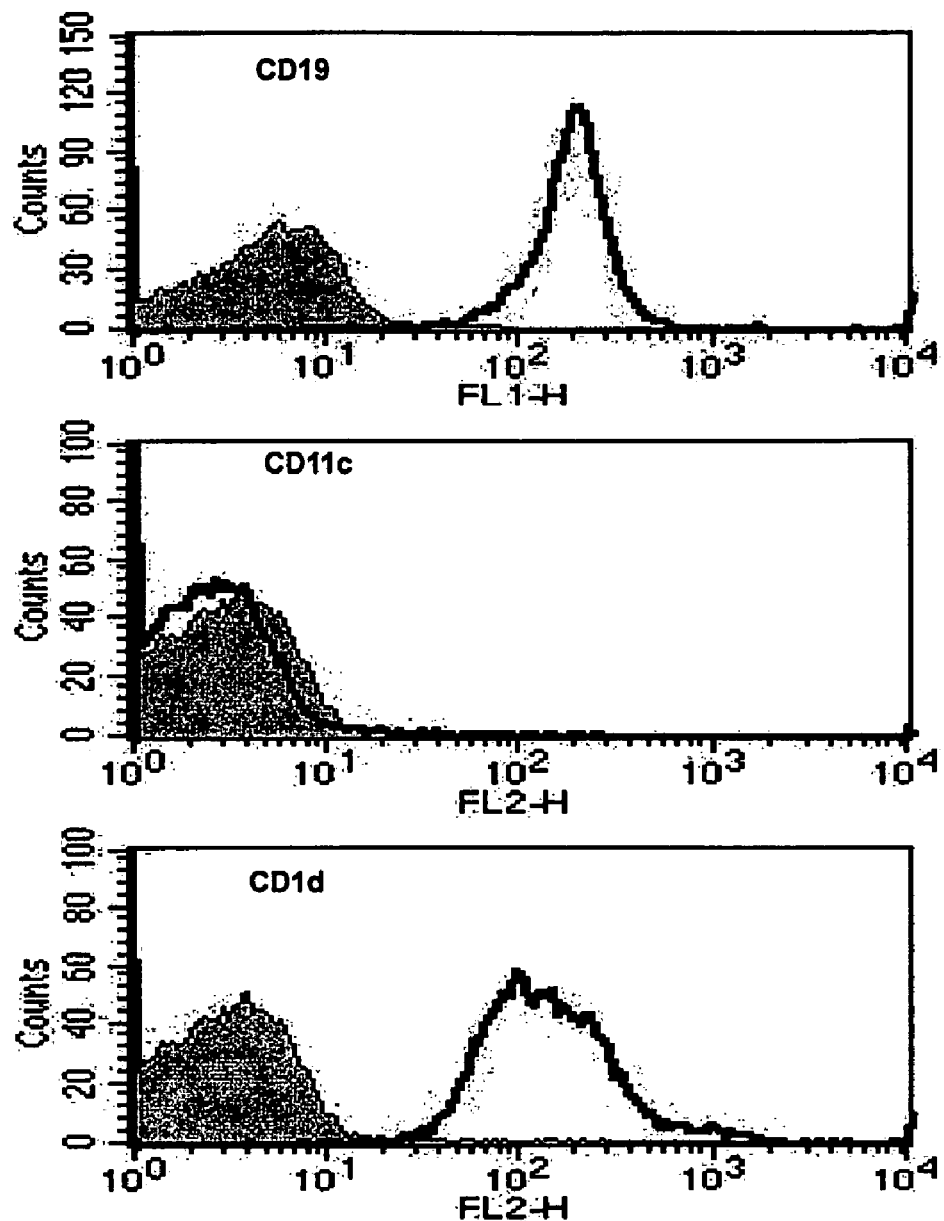

[Fig. 2]
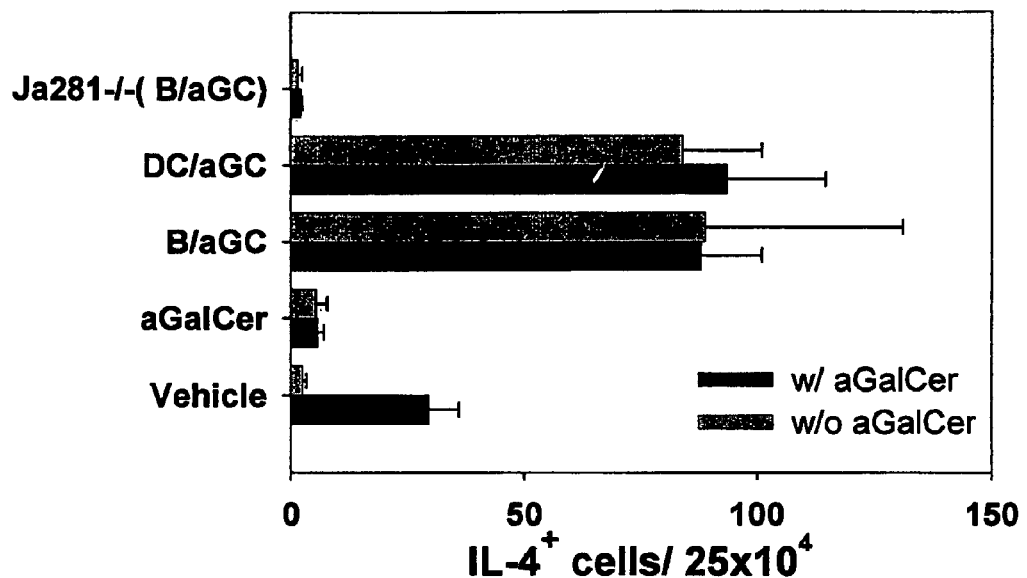
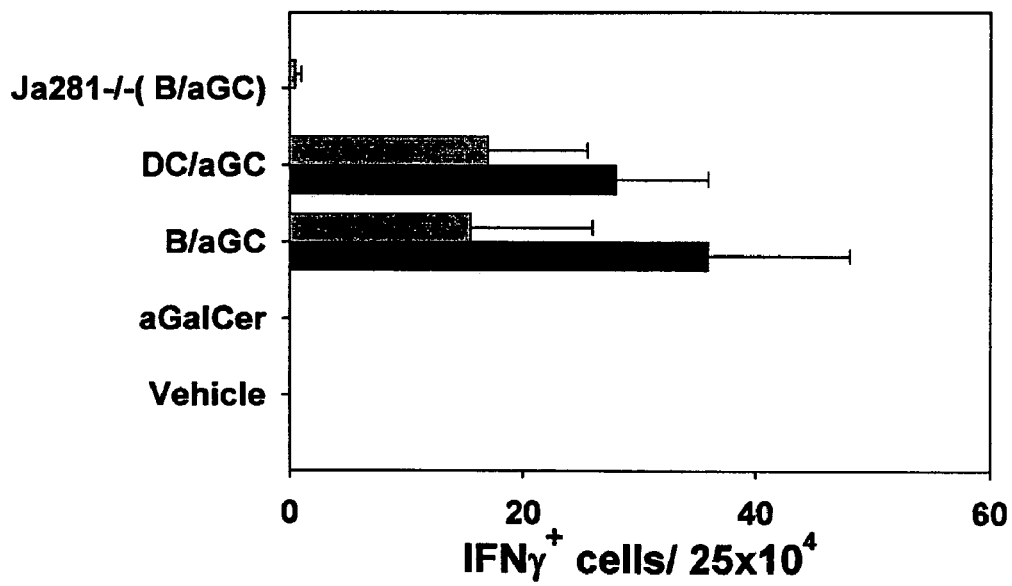

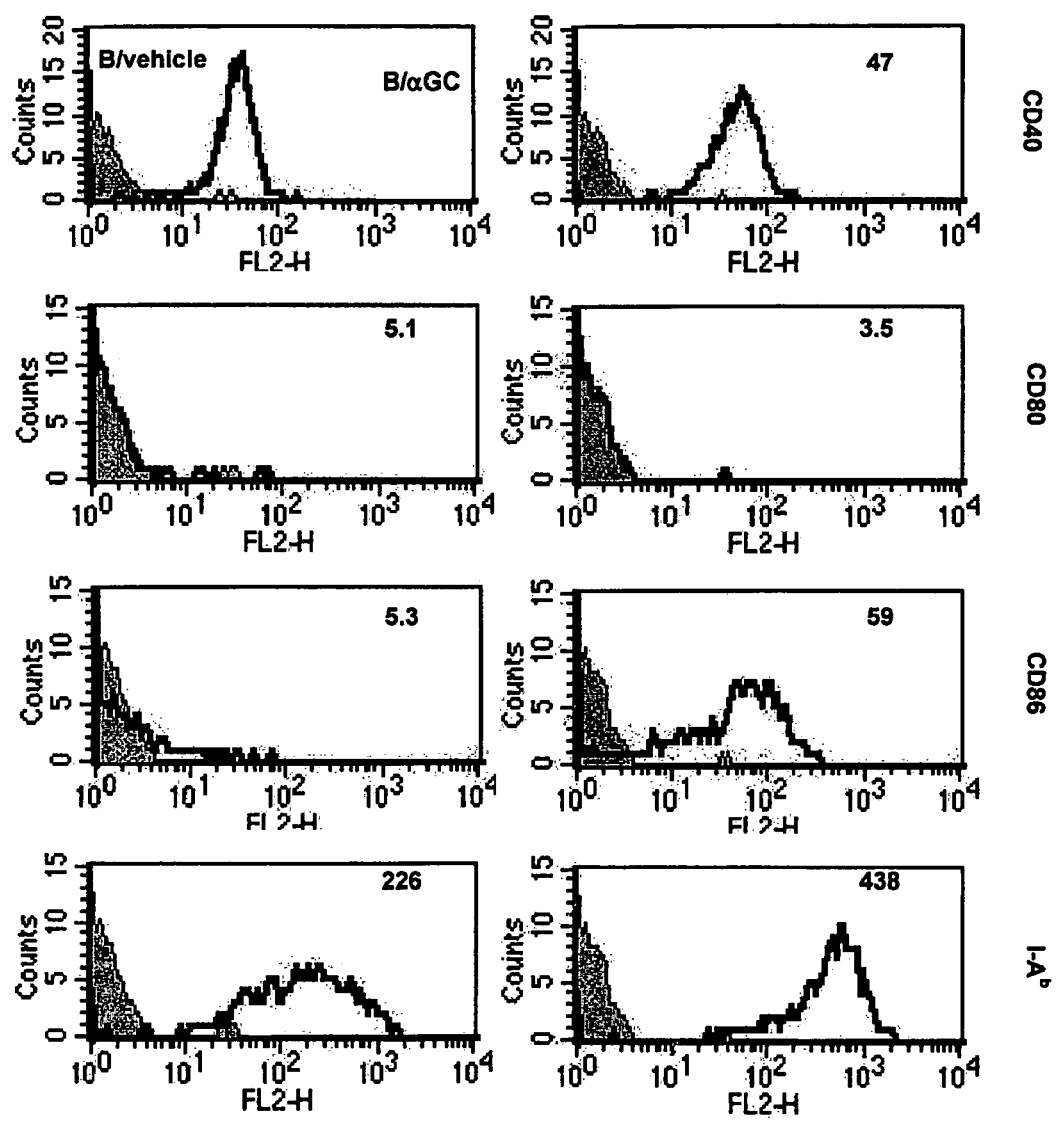
[Fig. 3]

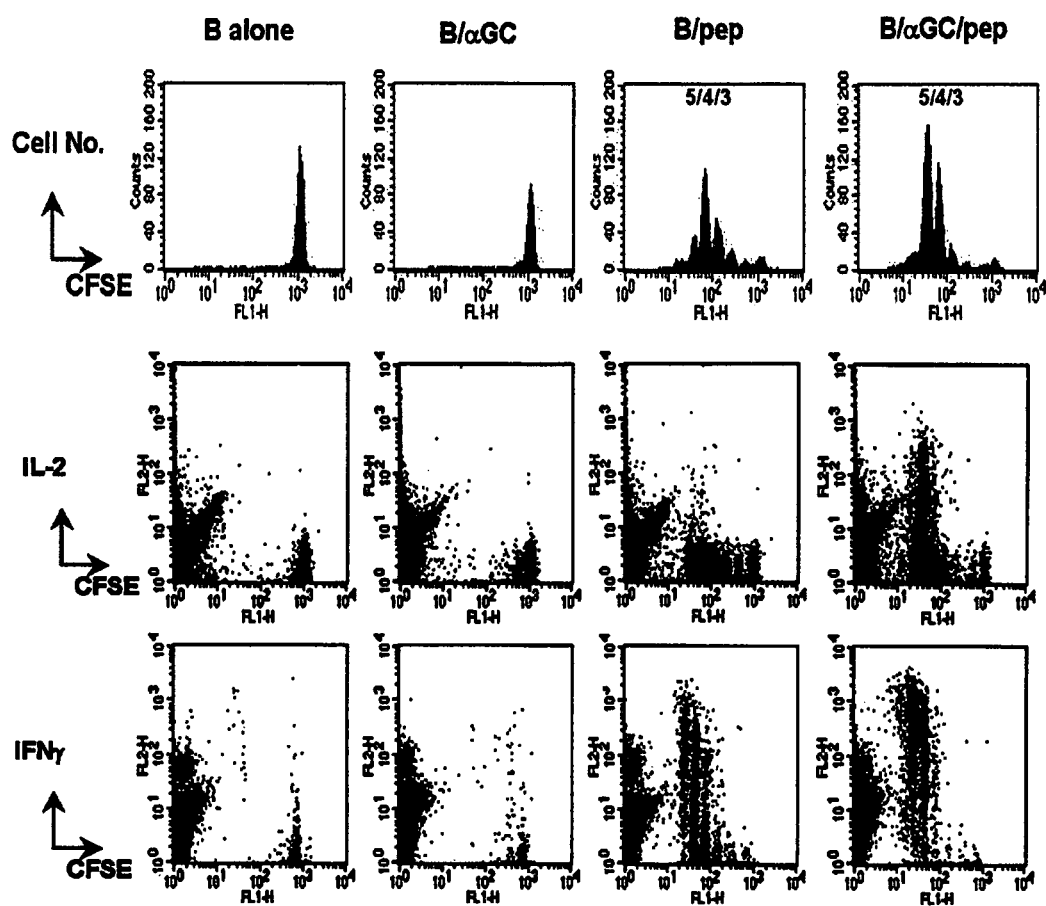

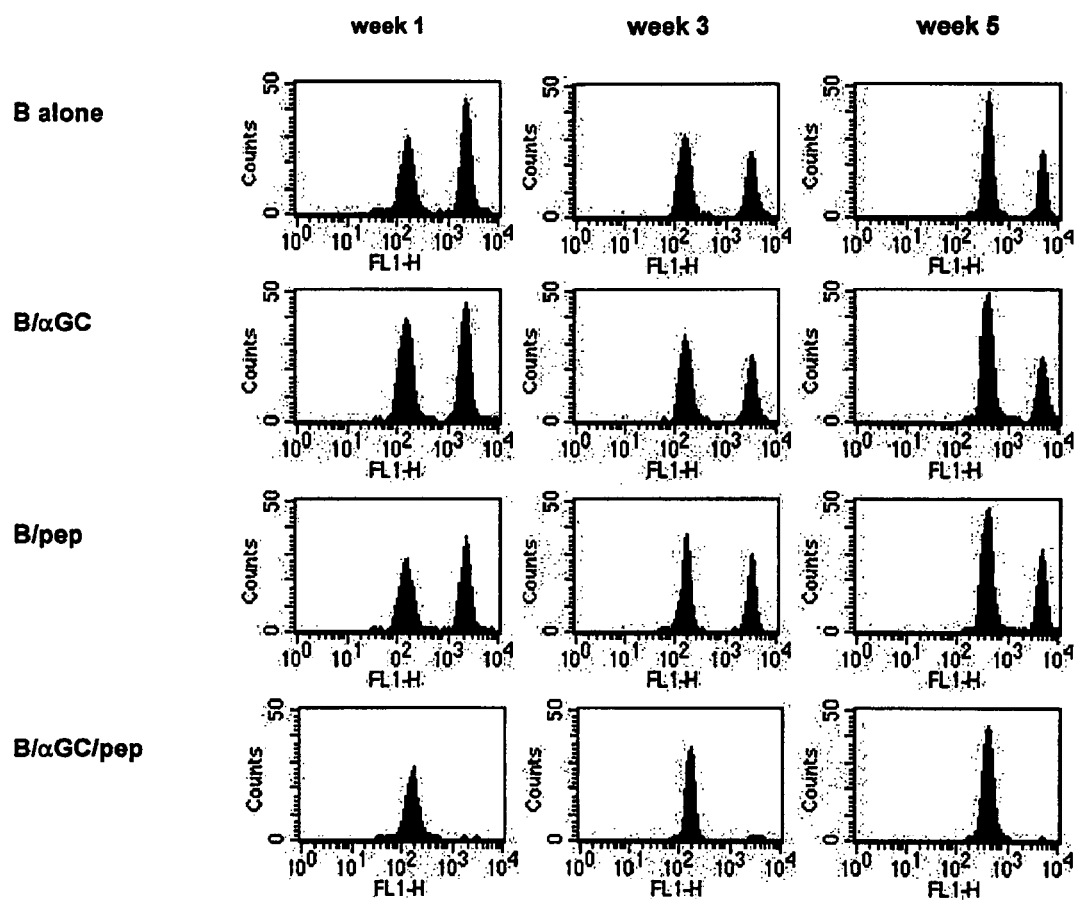
[Fig. 5]

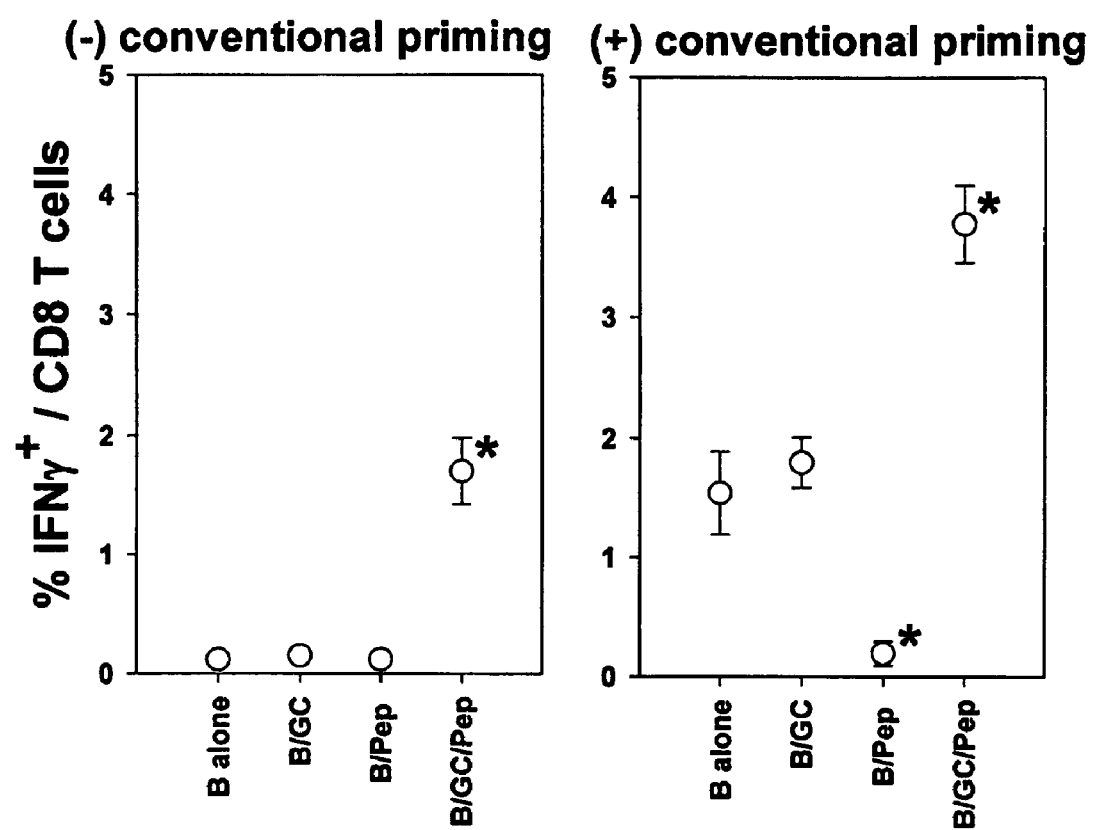
[Fig. 6]

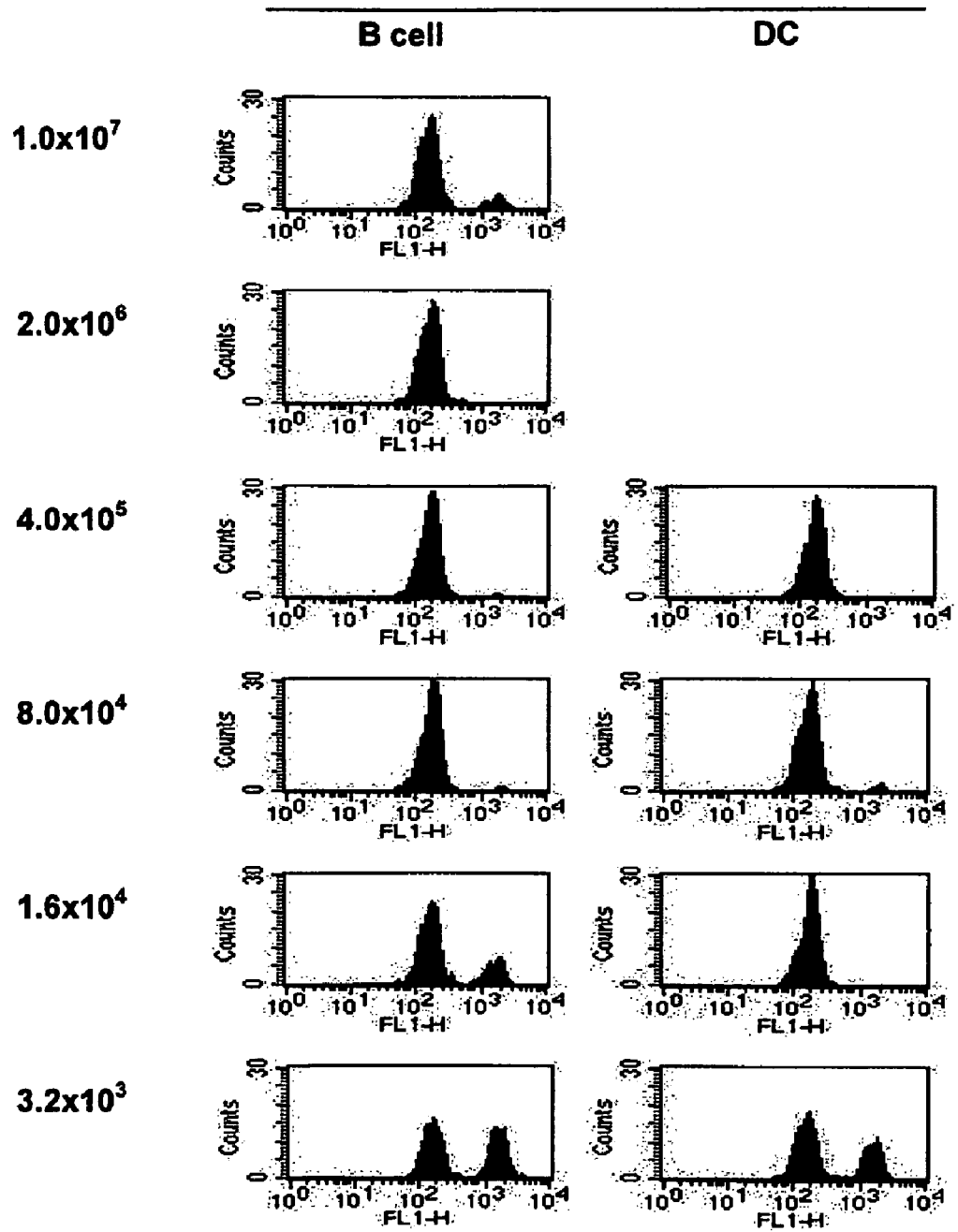

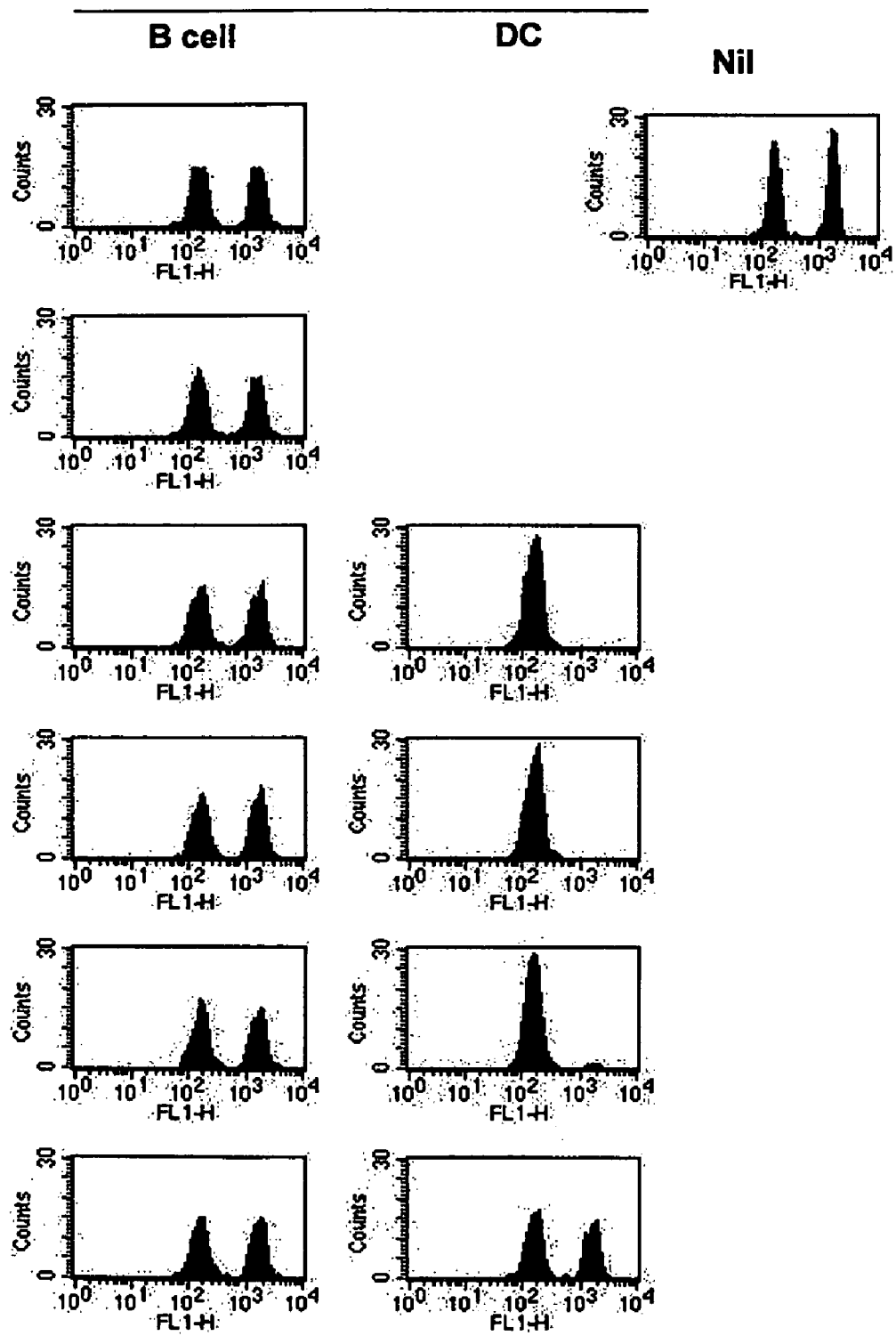
[Fig. 8]

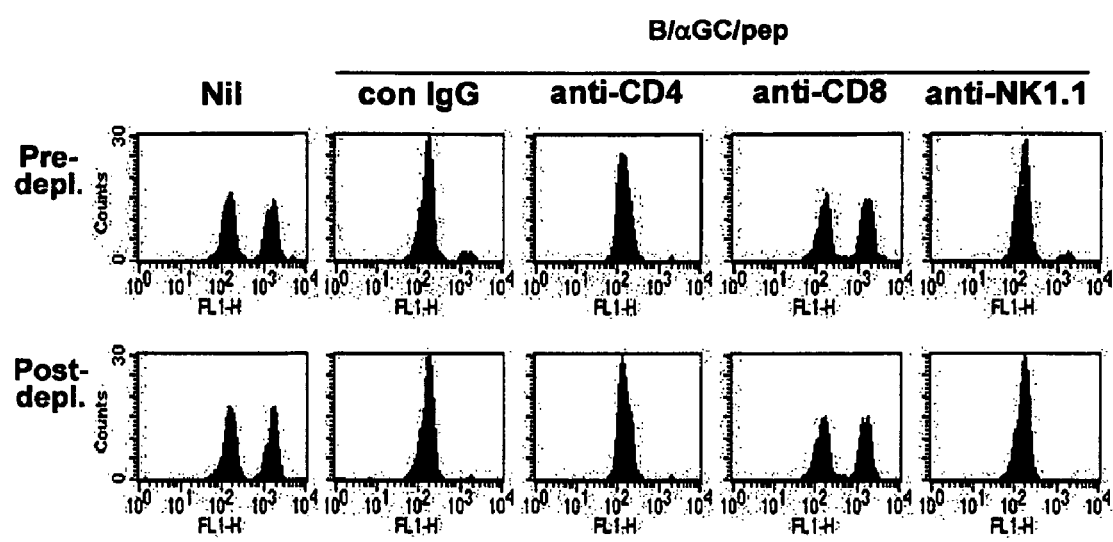
[Fig. 9]

[Fig. 10]
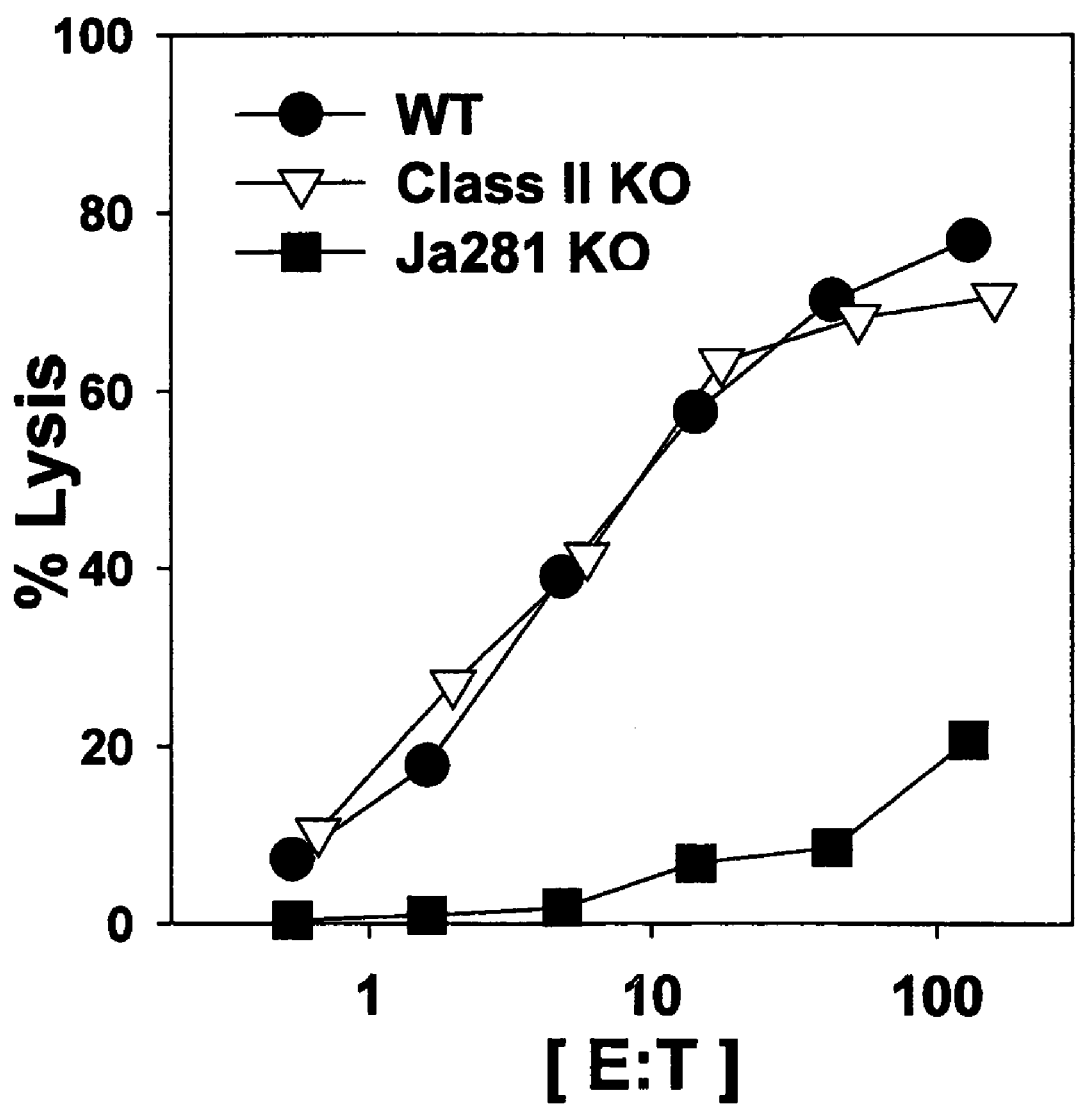

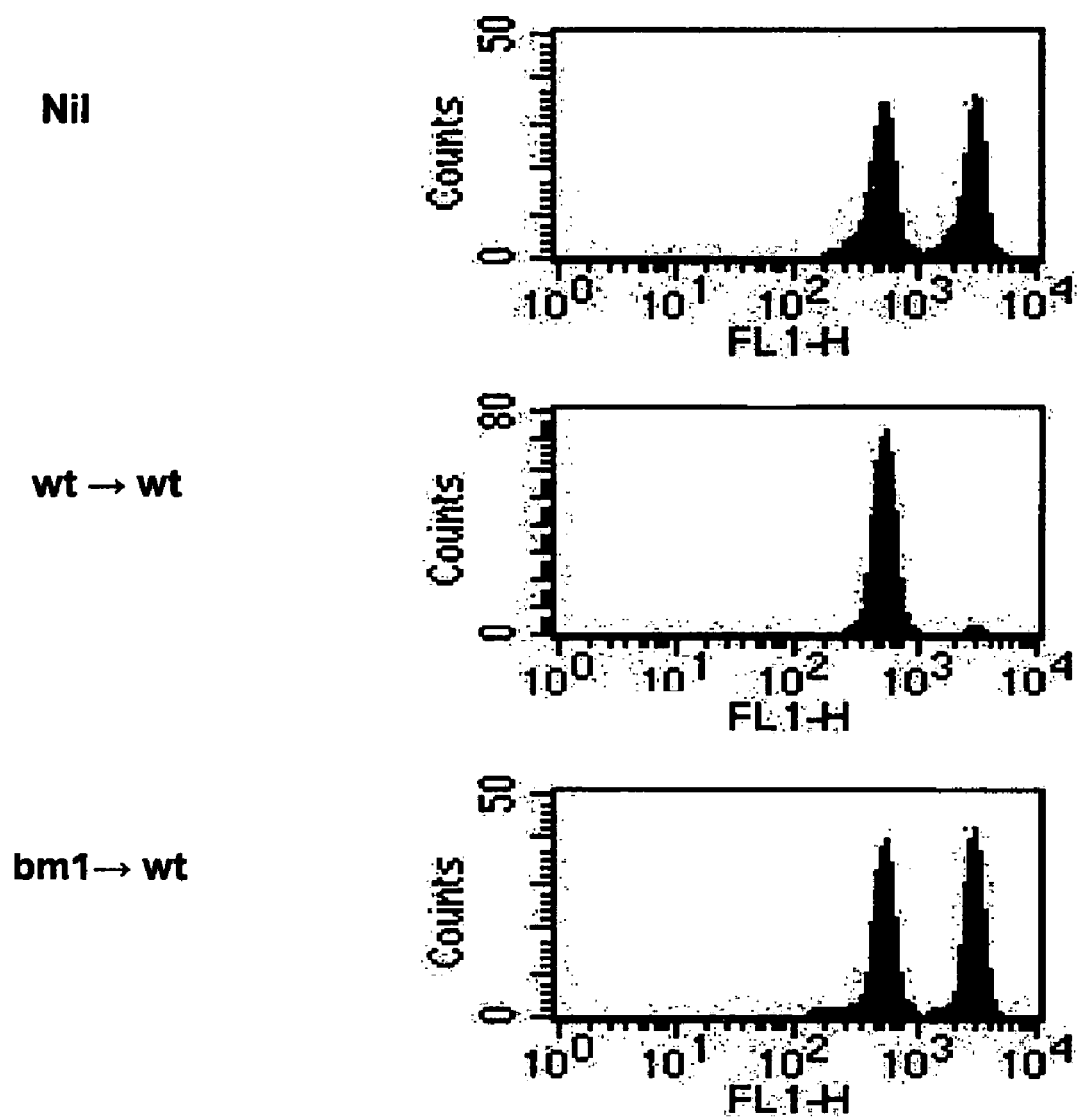

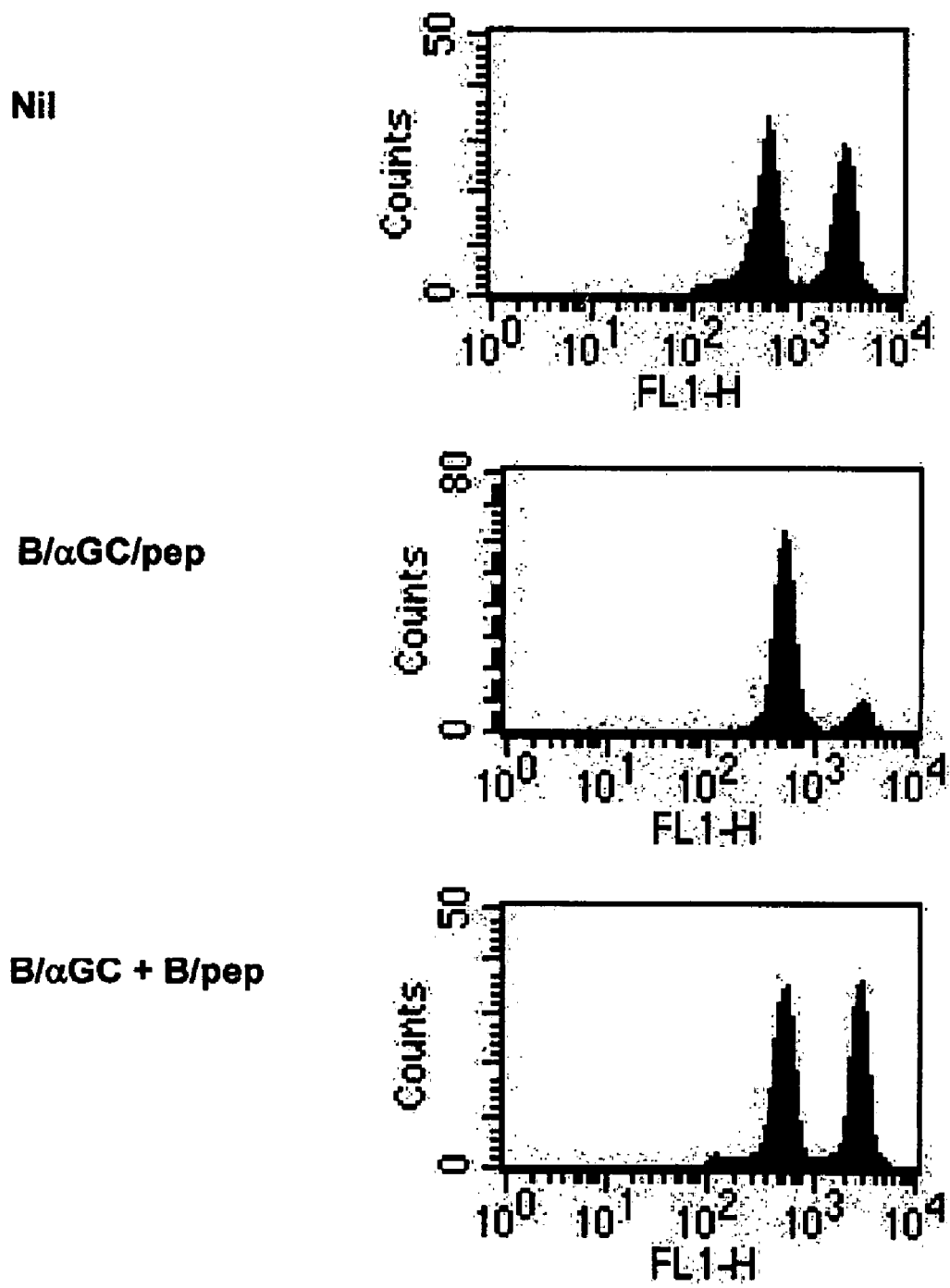

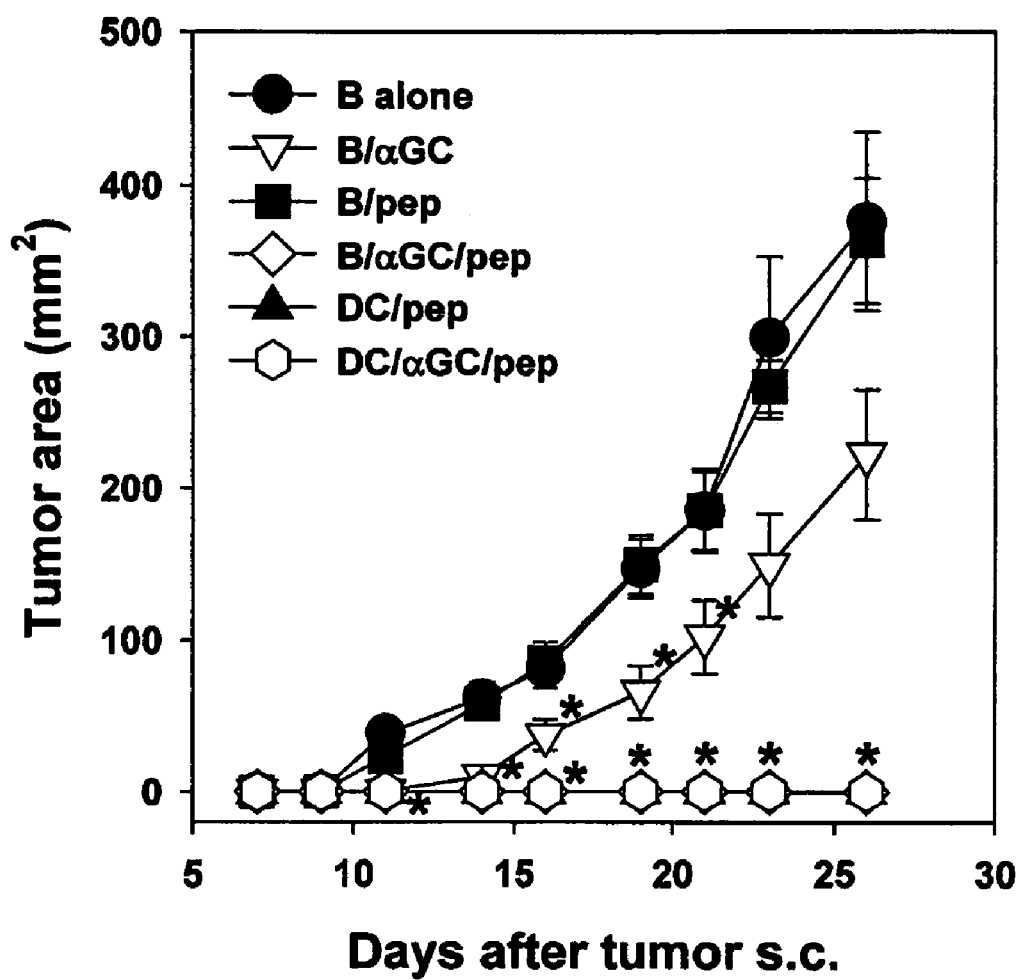
[Fig. 13]

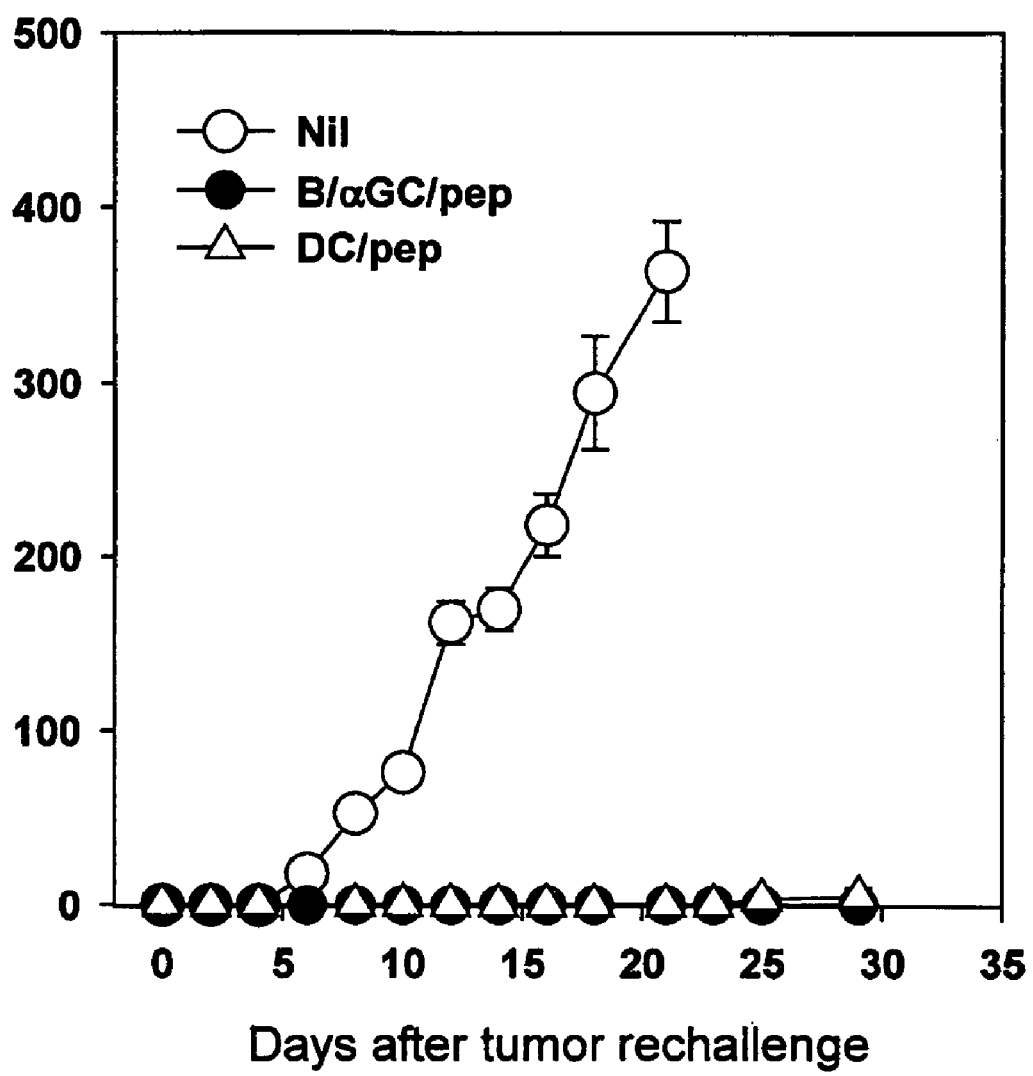

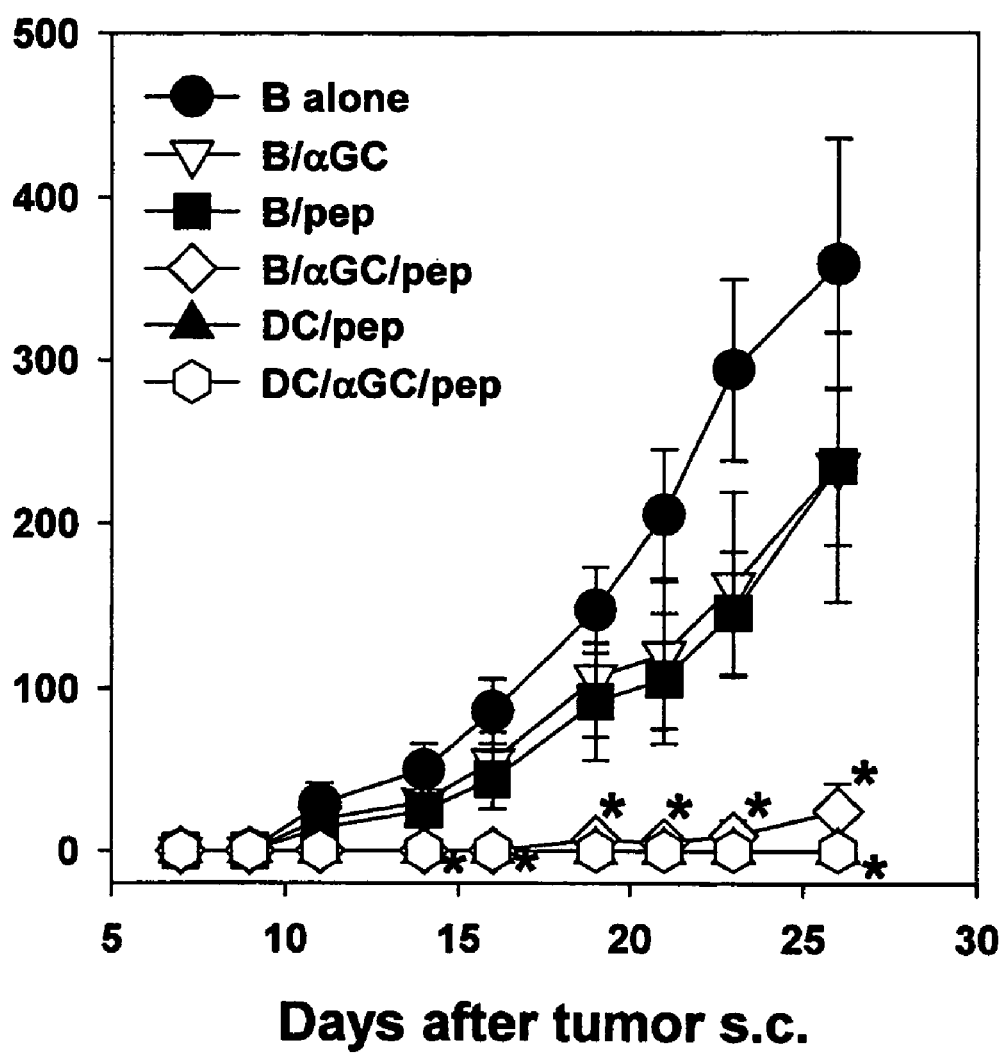

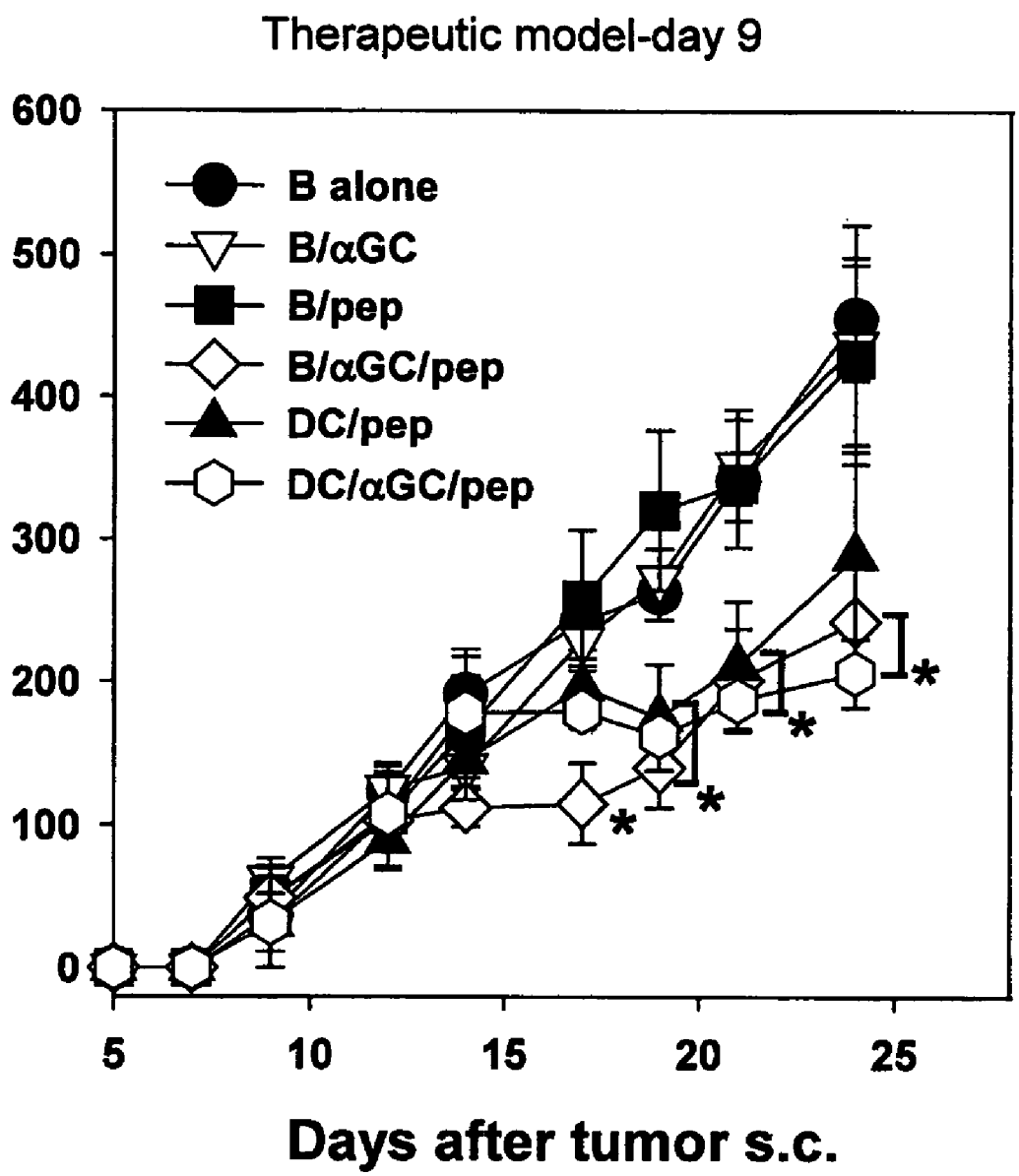
[Fig. 16]

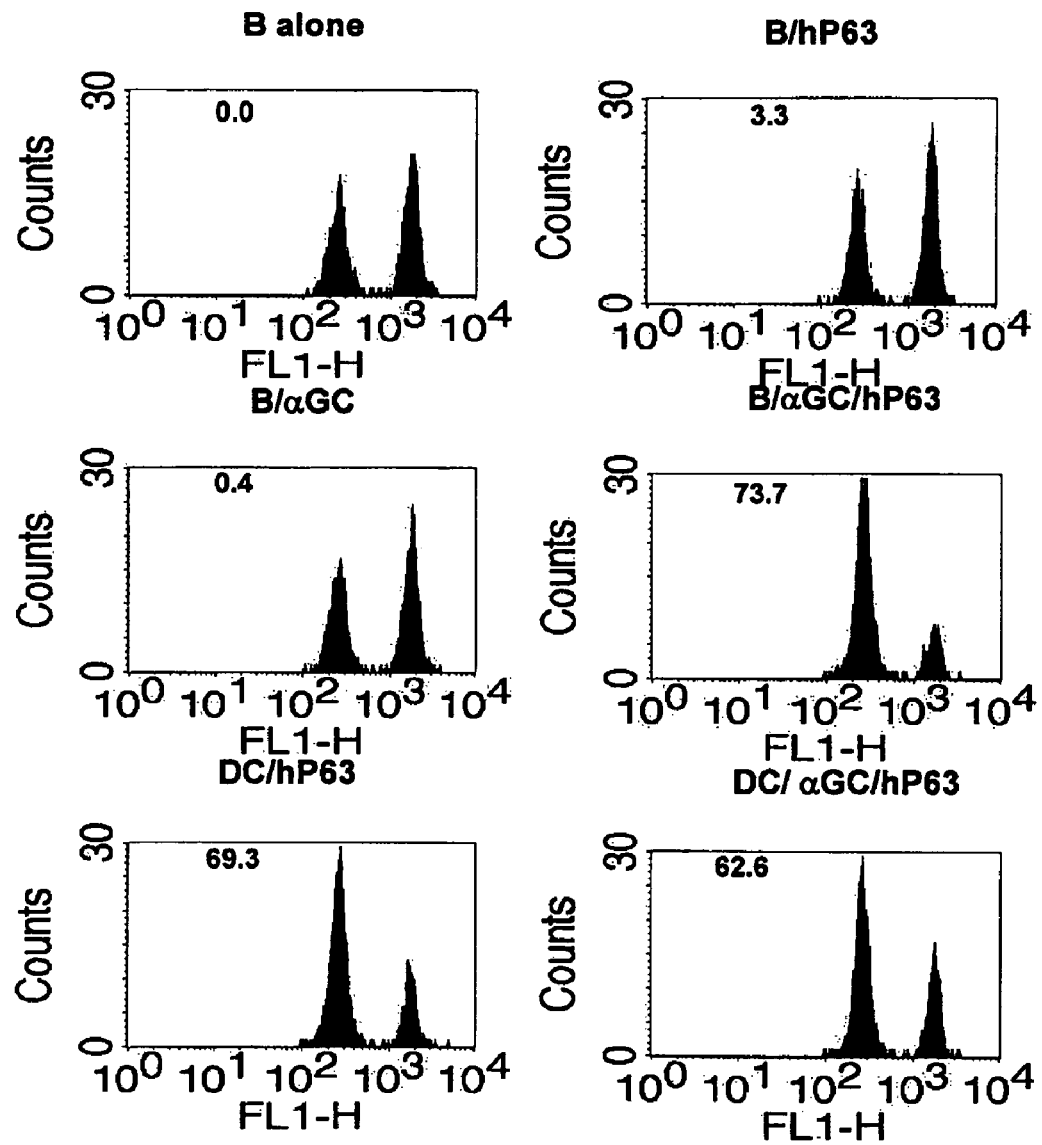
[Fig. 17]

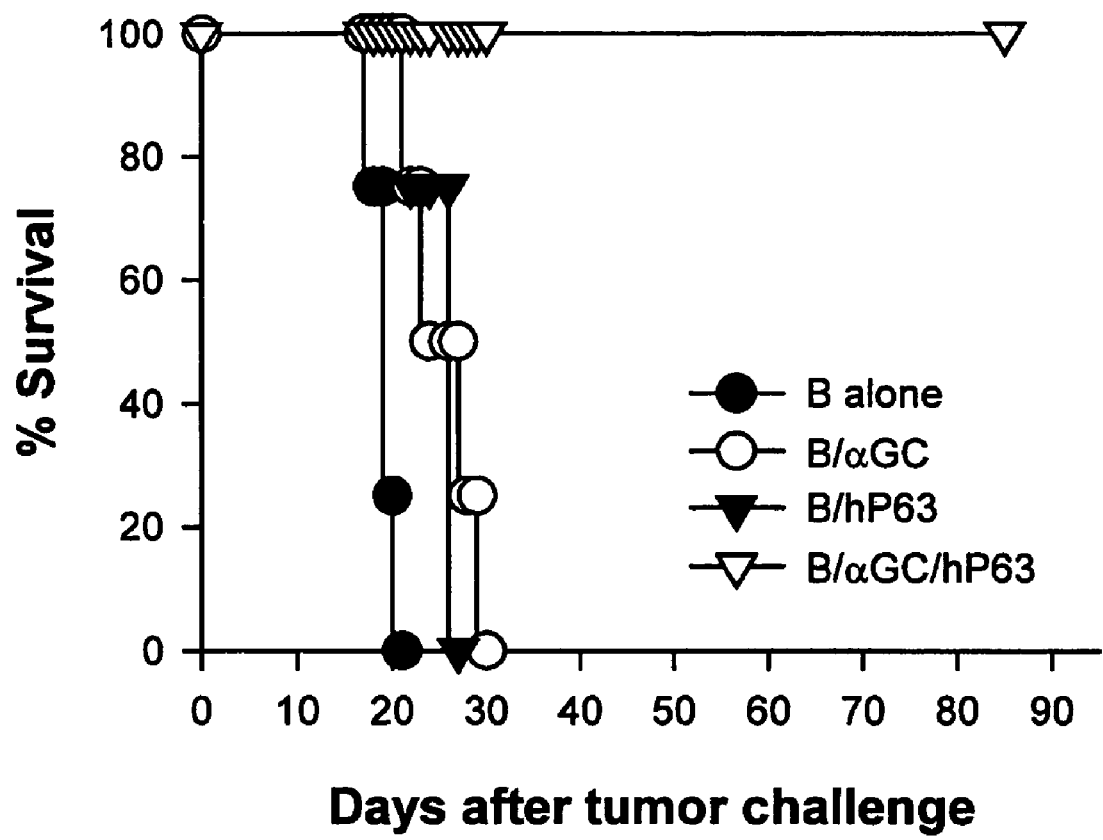
[Fig. 18]

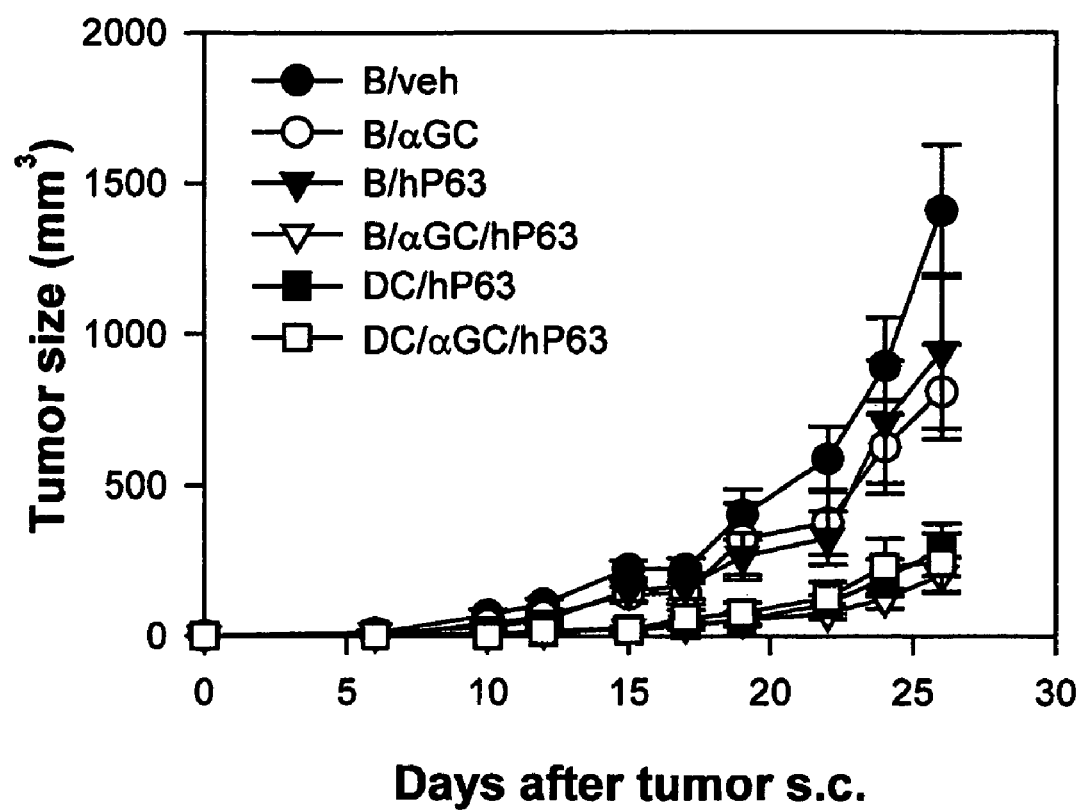
[Fig. 19]

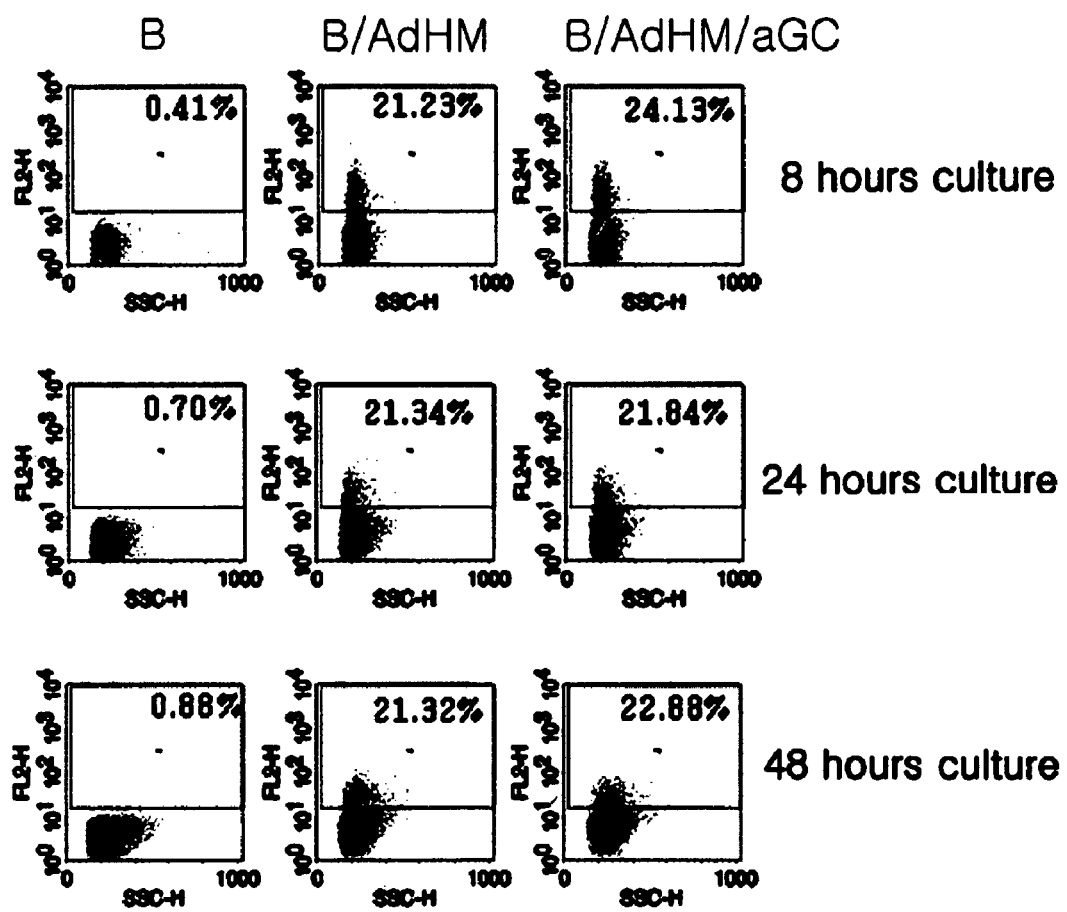
[Fig. 20]

[Fig. 21]
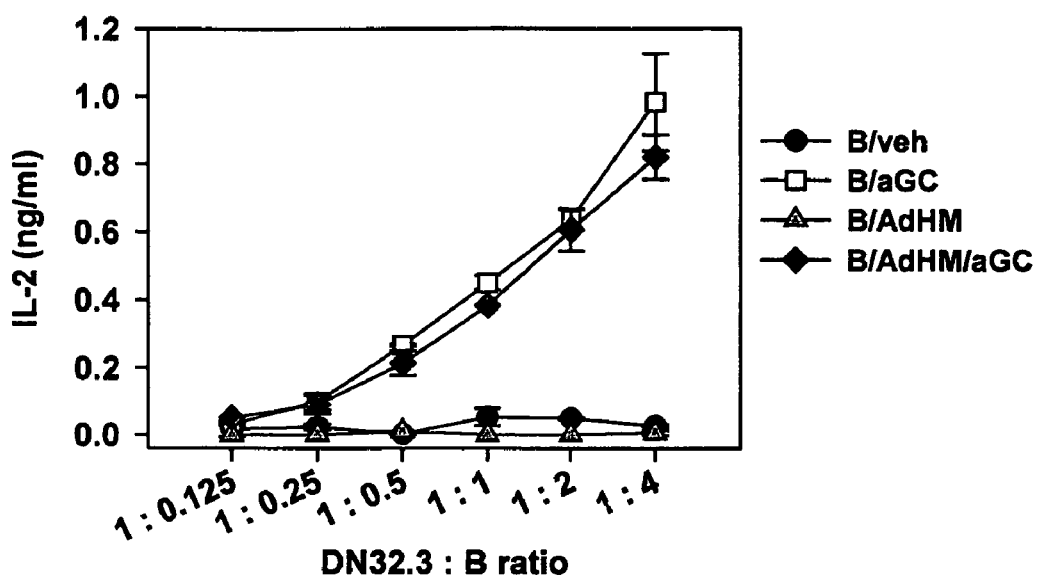
[Fig. 22]
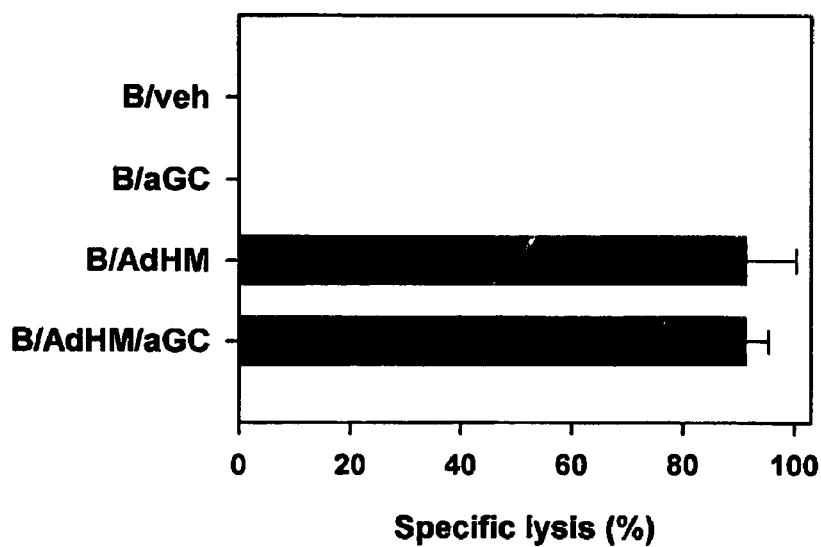

[Fig. 23]
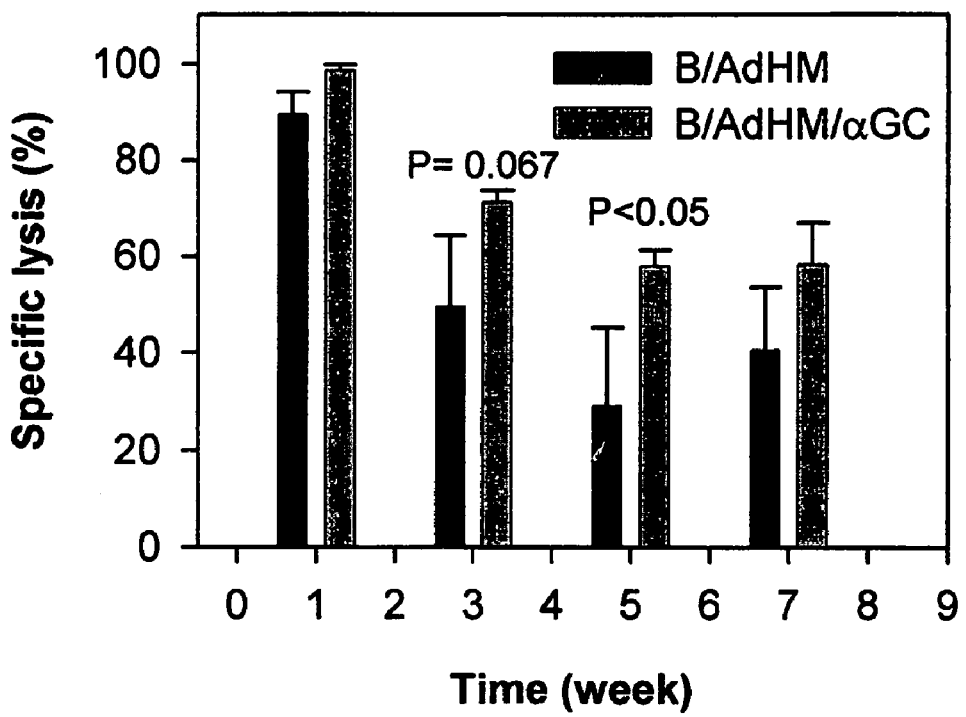
[Fig. 24]
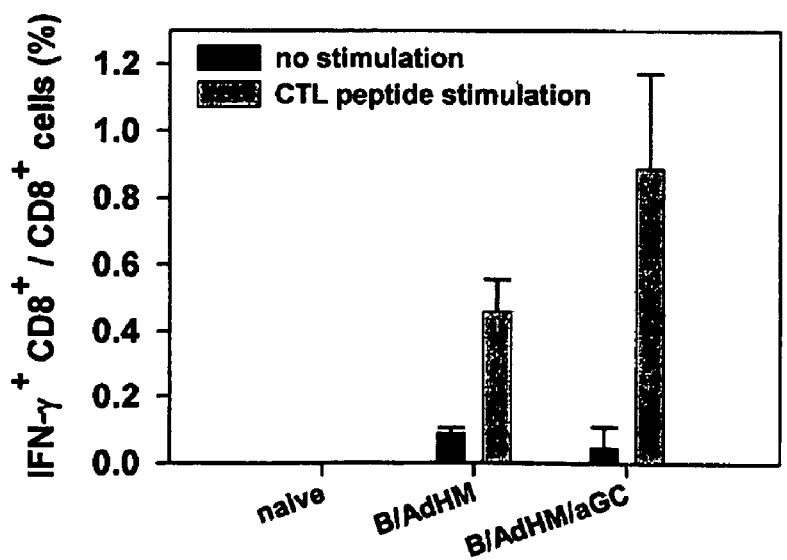

[Fig. 25]
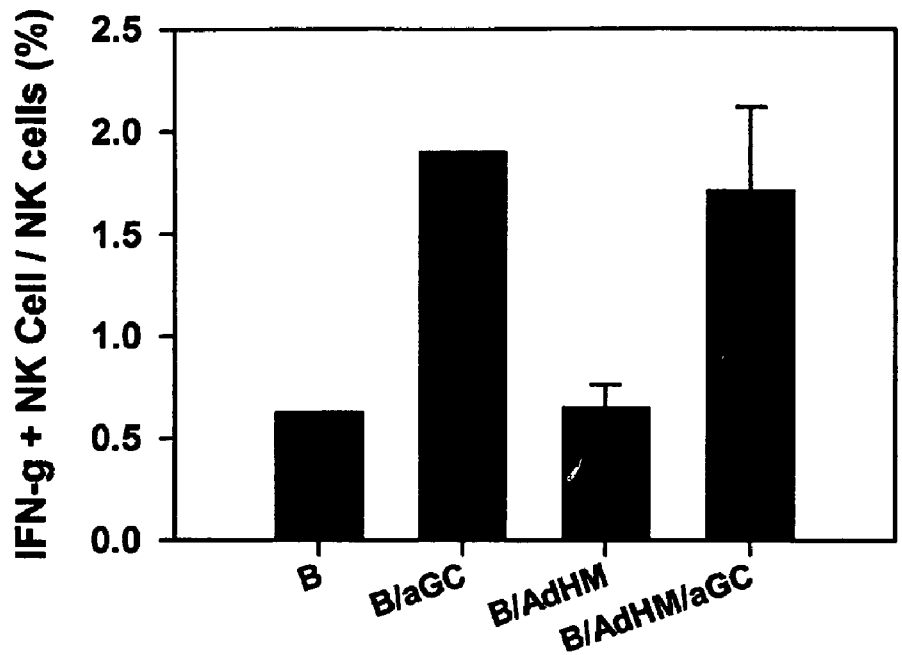
[Fig. 26]
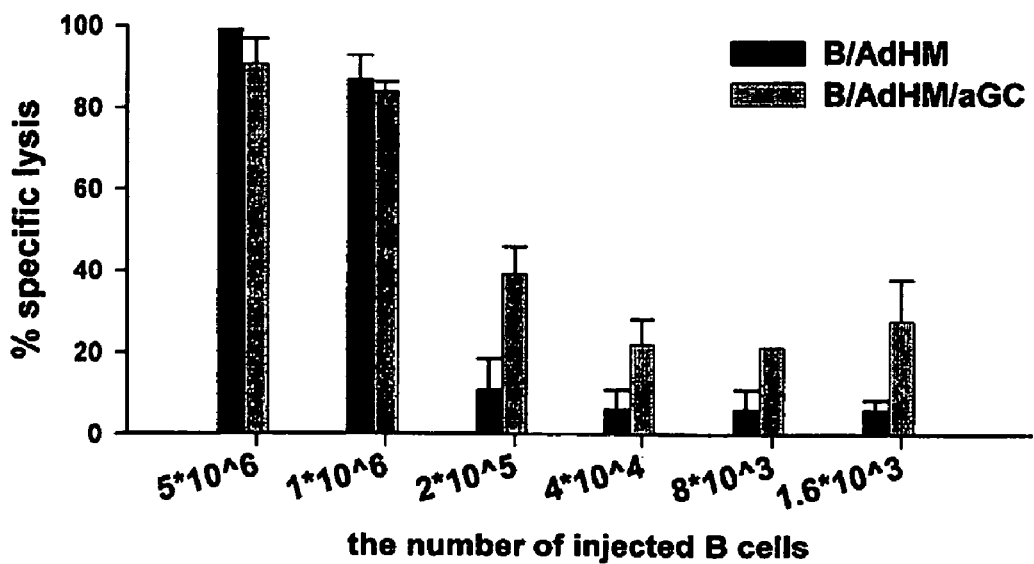

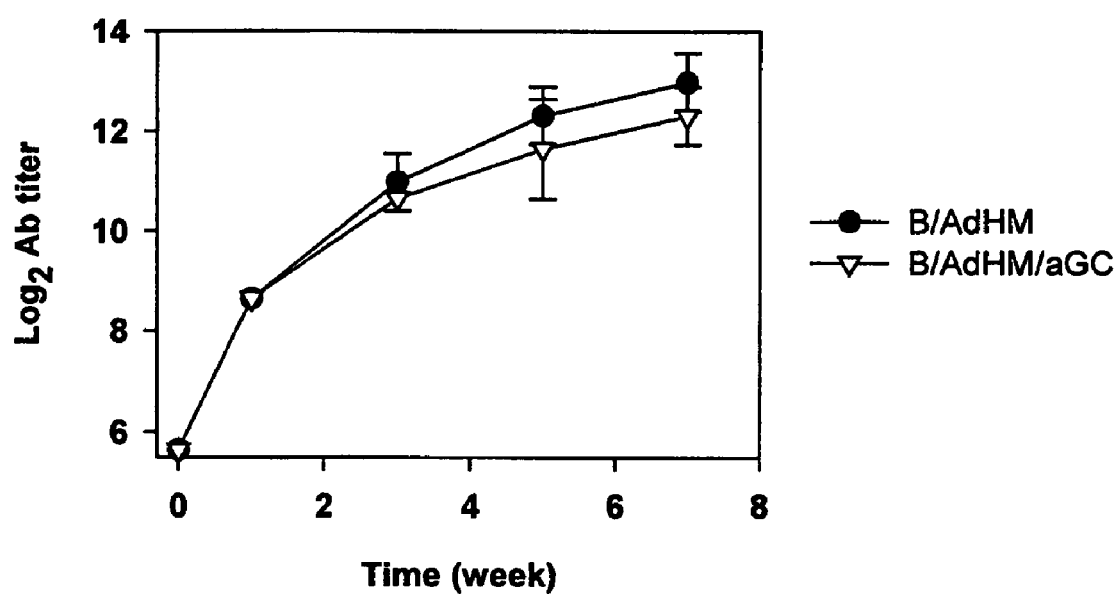
[Fig. 27]

[Fig. 28]
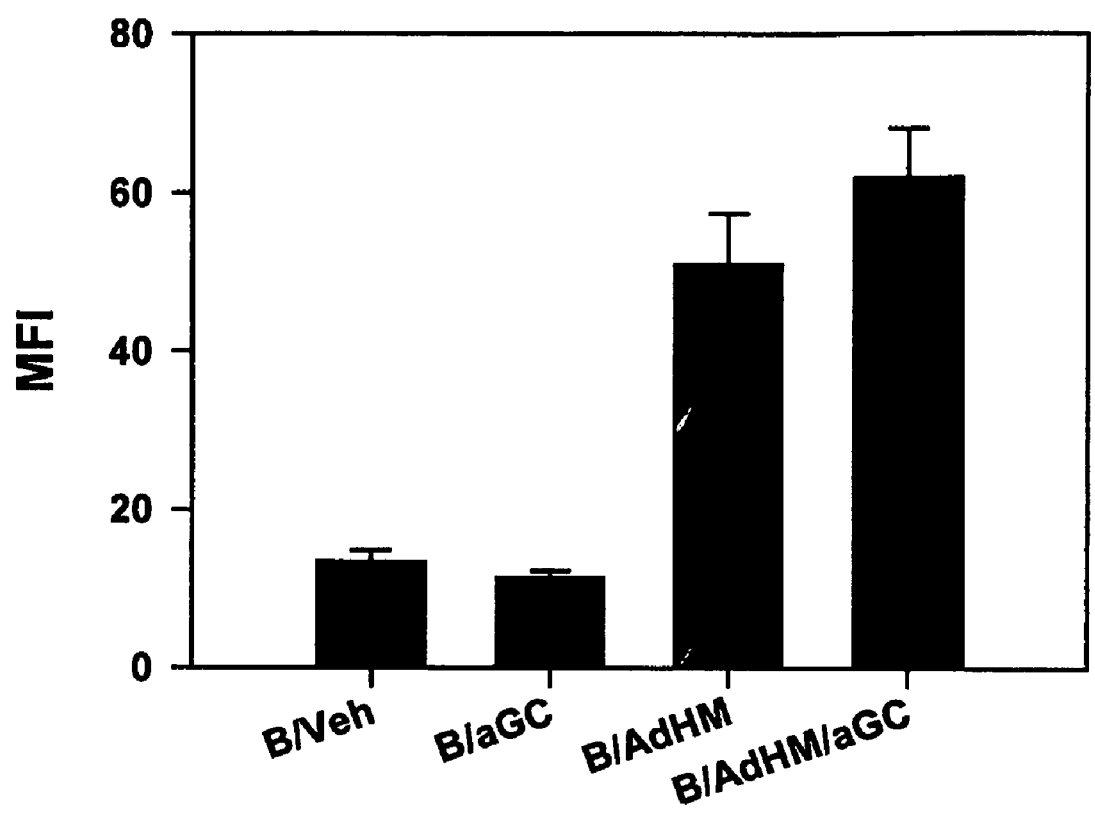

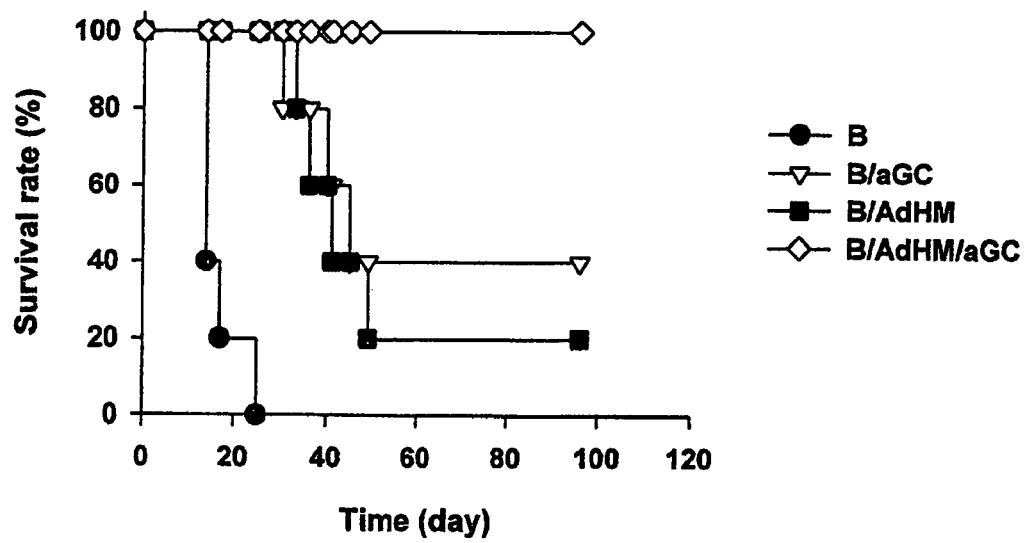
[Fig. 29]
Prevention Effect
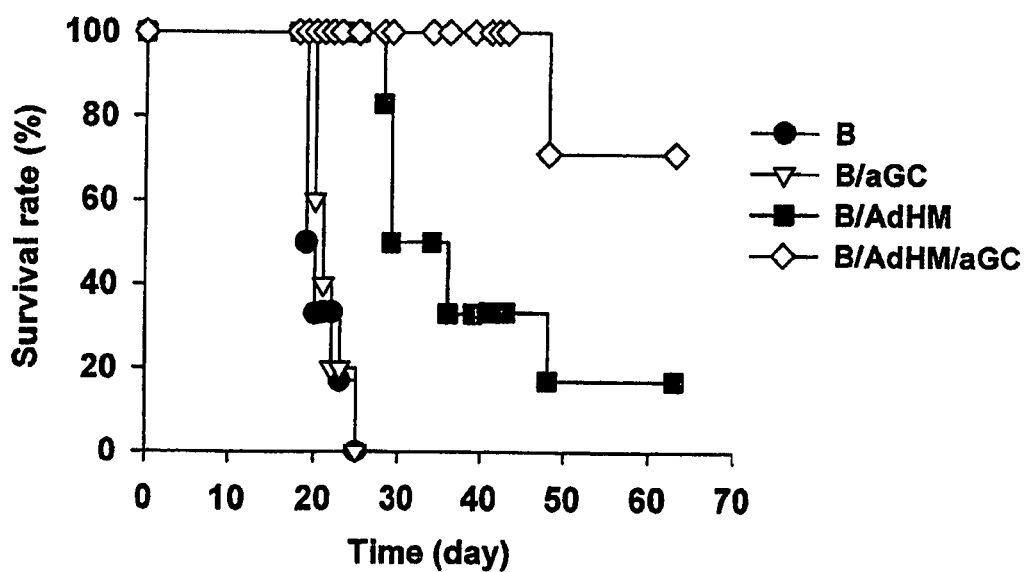
Therapeutic effect

[Fig. 30]
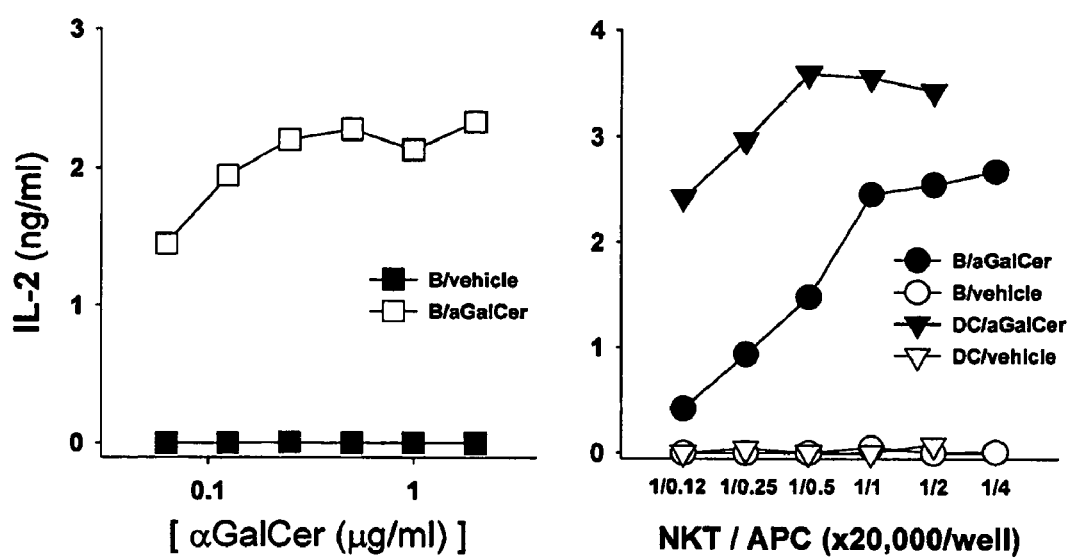

[Fig. 31]
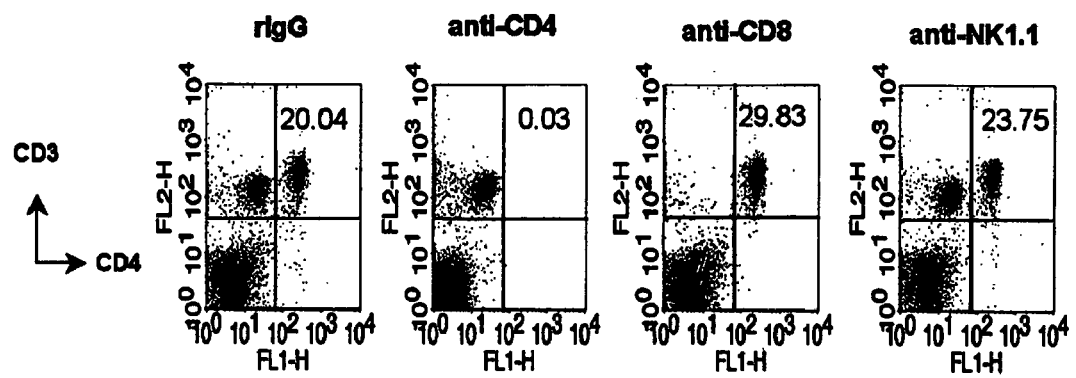
[Fig. 32]
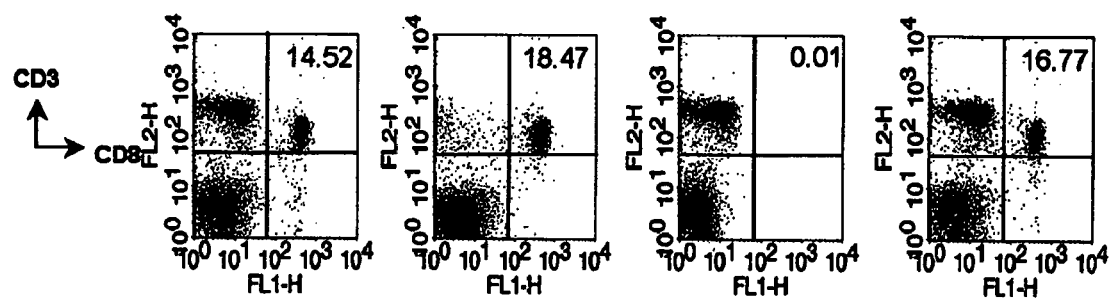

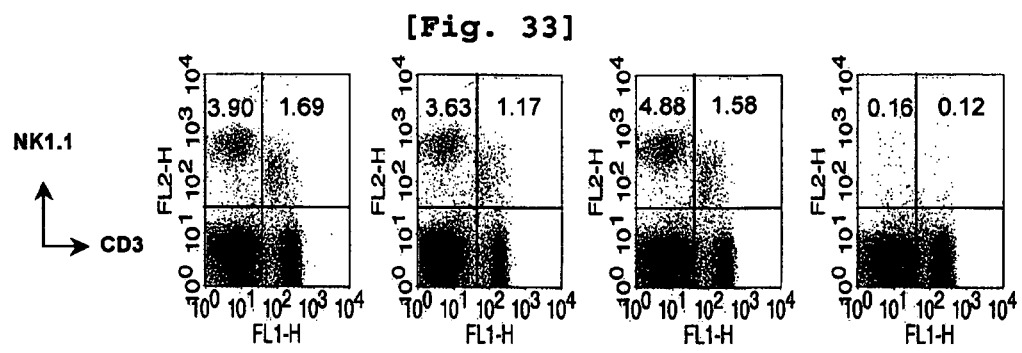
[Fig. 33]
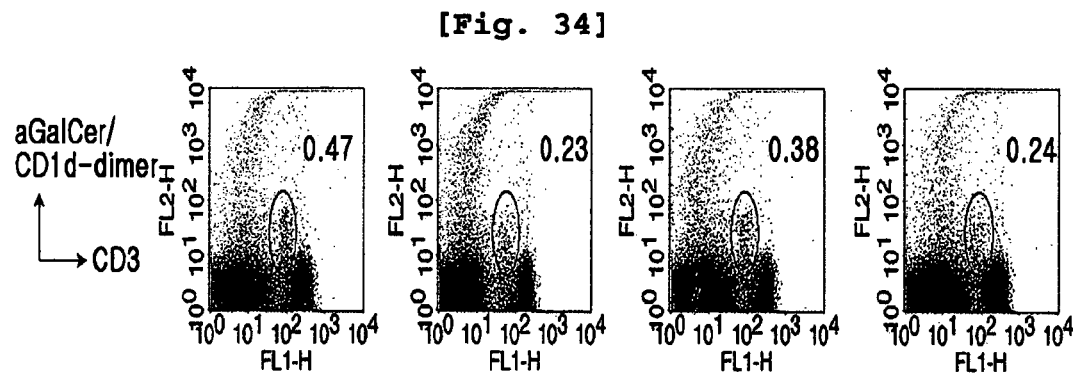
[Fig. 34]

[Fig. 35]
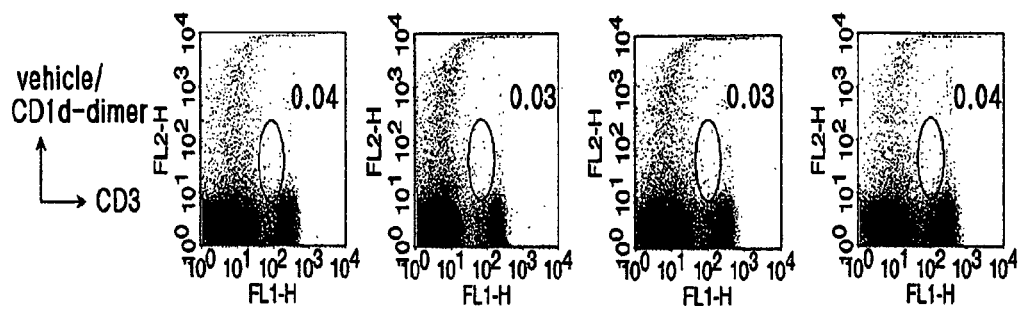
[Fig. 36]
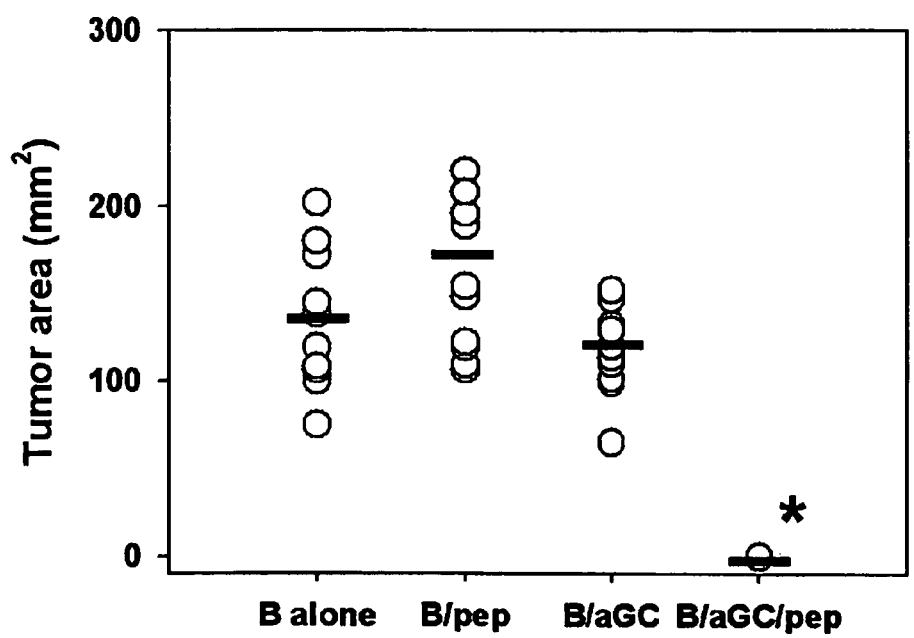

B CELL-BASED VACCINE LOADED WITH THE LIGAND OF NATURAL KILLER T CELL AND ANTIGEN

FIELD OF THE INVENTION

The present invention relates to a B cell-based vaccine loaded with the ligand of natural killer T cell and antigen for the prevention and treatment of infectious disease and cancer, more precisely, an immuno-therapeutic and prophylactic vaccine mediated by B cells loaded with α-galactosylceramide, a kind of glycolipid which can stimulate natural killer T cell, together with antigen.

BACKGROUND OF THE INVENTION

In general, tumor antigens cannot be efficiently presented by an antigen presenting cell, that is, immune response is not effectively induced. An antitumor vaccine is a novel therapeutic vaccine which is characterized by activating tumor specific immune system (for example, introducing tumor antigens to antigen presenting cells) to induce a strong immune response to destroy cancer cells.

Of the available vaccine approaches, cellular vaccines using antigen presenting cells (APC) such as dendritic cells (DC) are known to be reliable at generating effective T cell immunity (Rosenberg, S. A. et al., Nat. Med., 10, 909-915, 2004). Because DC-based vaccines in particular have been shown to efficiently induce Ag-specific effector and memory T cells, they are being considered for antitumor immunotherapy in a number of clinical trials (Rosenberg, S. A. et al., Nat. Med., 10, 909-915, 2004). Dendritic cells are ideal antigen-presenting cells (APC) for immunotherapy because they can capture Ag and then migrate into lymphoid organs, where they present the Ag to the relevant T cell. More importantly, they provide strong co-stimulation to the T cells (Figdor, C. G. et al., Nat. Med., 10, 475-480, 2004; and Banchereau, J. et al., Cell, 106, 271-274, 2001). The DC-vaccine approach is well-established for both experimental and clinical studies. However, DCs are relatively sparse in blood and lymphoid tissues and it is difficult to increase their numbers ex vivo from blood monocytes, both of which present major drawbacks to their widespread use in vaccines (Schultze, J. L. et al., Trends Immunol., 25, 659-664, 2004).

B cells offer an attractive alternate source for cellular vaccines in that they are abundant in lymphoid tissues and blood, and easily expanded ex vivo (Schultze, J. L. et al., Trends Immunol., 25, 659-664, 2004; von Bergwelt-Baildon, M. S. et al., Blood, 99, 3319-3325, 2002; and Schultze, J. L. et al., J. Clin. Invest., 100, 2757-2757, 1997), and home to lymphoid organs after parenteral administration.

Despite these advantages, B cells have been ignored as a source of the cellular vaccine since they are poorly immunogenic. In fact, accumulating evidence shows that they induce immune tolerance in both CD4 and CD8 T cells directly, probably due to the lack of co-stimulation (Bennett, S. R. et al., J. Exp. Med., 188, 1977-1983, 1998; and Eynon, E. E. et al., J. Exp. Med., 175, 131-138, 1992). However, 'activated'. B cells can prime both CD4 and CD8 T cells (von Bergwelt-Baildon, M. S. et al., Blood, 99, 3319-3325, 2002; Schultze, J. L. et al., J. Clin. Invest., 100, 2757-2765, 1997; Lapointe, R. et al., Cancer Res., 63, 2836-2843, 2003; and Heit, A. et al., J. Immunol., 172, 1501-1507, 2004), suggesting that, when activated by the appropriate stimuli, B cells can act as immunogenic APC capable of inducing Ag-specific T cell immunity.

It is well established that iNKT cells play a crucial role in a variety of immune responses and in immunopathology as a whole. Although they represent less than 1% of lymphocytes in mice, iNKT cells govern the response to self- and exogenous-Ag and determine whether tolerance or immunity is induced (Kronenberg, M., Annu. Rev. Immunol., 23, 877-900, 2005; and Park, S. H. & Bendelac, A., Nature, 406, 788-792, 2000). They act as suppressors of immunity in tumor, diabetes and at immune-privileged site (Sonoda, K. H., et al., J. Exp. Med., 190, 1215-1226, 1999).

In contrast, ligand-mediated activation of iNKT cells lead to the activation of T, B, and NK cells as well as DC. Injection of αGalCer, an iNKT ligand, generates antitumor immunity via the mediation of NK and T cells (Moodycliffe, A. M., et al., Nat. Immunol., 1, 521-525, 2000).

Alpha-galactosylceramide (αGalCer) is a kind of glycolipid extracted from marine sponge, which is the ligand of natural killer T cell having Vα14+ T cell receptor (TCR) and presented by CD1d on an antigen presenting cell (APC) (Kawano et al., Science, 278: 1626, 1997). The activation of the natural killer T cells leads to the mass-production of IFN-γ and IL-4, by which immune responses against either infectious disease or cancer can be controlled (Chen et al., J. Immunol., 159: 2240, 1997; Wilson et al., Proc. Natl. Acad. Sci. U.S.A., 100: 10913, 2003).

Mice to which protein Ag and αGalCer have been coadministered develop humoral and cell-mediated immunity including cytotoxic T cell responses (Hermans, I. F., et al., J. Immunol, 171, 5140-5147, 2003; and Stober, D. et al., J. Immunol., 170, 2540-2548, 2003). Furthermore, a recent study has demonstrated that αGalCer-loaded DC generate longer-lasting iNKT cell responses than does free-form of αGalCer, suggesting that the adjuvancity of iNKT-ligands could be enhanced by targeting it to professional APC.

The present inventors confirmed that presentation of the iNKT-ligand on B cells could convert them from tolerogenic to immunogenic, thereby generating strong immunity against Ag displayed on MHC molecules of the B cells. To verify the confirmation and thereby to complete this invention, the present inventors further confirmed the efficiency of αGalCer-loaded, peptide-pulsed B cells and αGalCer-loaded, adenovirus-transduced B cells in generating antigen specific immunity and anti-tumor activity.

DISCLOSURE

Technical Problem

It is an object of the present invention to provide an immunotherapeutic/prophylactic vaccine and an antitumor vaccine that is able to induce antigen-presenting B cell-mediated antigen-specific immune responses. Natural killer T cells stimulated with αGalCer on CD1d molecule of antigen-loaded B cells convert tolerogenic B cells into immunogenic antigen presenting cells.

Technical Solution

The present invention provides an immunotherapeutic/prophylactic vaccine and an antitumor vaccine mediated by B cells loaded with the ligand of natural killer T cell and antigen.

The present invention also provides an antitumor vaccine mediated by B cells loaded with the ligand of natural killer T cell and expressing a tumor antigen.

The present invention further provides a natural killer T cell activator mediated by αGalCer loaded B cells.

In addition, the present invention provides a cytotoxic response inducer mediated by tumor antigen expressing B cells.

Hereinafter, the present invention is described in detail.

The present invention provides an immunotherapeutic/prophylactic vaccine and an antitumor vaccine mediated by B cells loaded with the ligand of natural killer T cell alone or with antigen.

The ligand of natural killer T cell includes alpha-galacturonosylceramide and alpha-glucuronosylceramide originated from Sphingomonas spp. (Mattner, J. et al. Nature 434:525, 2005, Kinjo, Y. et al. Nature 434:520, 2005), phosphatidylinositoltetramannoside originated from M. tuberculosis (Fischer, K. et al. PNAS 101:10685, 2004), autoantigens isoglobotrihexosylceramide (Zhou, D. et al. Science 306:1786, 2004) and ganglioside GD3 (Wu, D. Y. et al. J. Exp. Med. 198:173, 2003), phosphatidylcholine (J. Immunol. 175:977, 2005), beta-galactosylceramide (βGalCer, Ortaldo J R et al. J. Immunol. 172:943), Leishmania surface glycosidic bond lipophosphoglycan and glycoinositol phospholipids (J. Exp. Med. 200:895, 2004), αGalCer derivatives beta-anomeric GalCer and alpha-anomeric GalCer (J. Immunol. 173:3693, 2004), αGalCer variants (J. Am. Chem. Soc. 126:13602, 2004) and bacteria lipid antigen such as glucose monomycolate originated from Nocardia falcinica (Moody, D. B. et al. J. Exp. Med. 192:965, 2000).

Since it was already well established that αGalCer-loaded DCs activate iNKT cells (van der Vliet H J, et al., J Immunol Methods., 1; 247(1-2):61-72, 2001), the present inventors examined whether αGalCer-loaded B cells would do likewise.

DCs and CD19+ B cells (FIG. 1) were isolated from a mouse. Each cell was pulsed with various concentrations of αGalCer then cocultured with an NKT hybridoma. Then, the level of IL-2 in the culture supernatant was measured. As a result, both αGalCer-loaded B cells (B/αGalCer) and αGalCer-loaded DC (DC/αGalCer) stimulated the NKT hybridoma to produce IL-2 (see FIG. 30). Therefore, it was confirmed that both B/αGalCer and DC/αGalCer can activate iNKT cells ex vivo.

To investigate whether B/αGalCer and DC/αGalCer administered in vivo could activate immune cells or not, the present inventors injected B/αGalCer or DC/αGalCer from C57BL/6 mice i.v. into syngenic mice and measured the level of IL-4- and IFN-γ-producing cells by ELISPOT. Particularly, wild type C57BL/6 or Jα281-/-mice were intravenously injected with vehicle, αGalCer, αGalCer-loaded B cells or αGalCer-loaded DC. One week later, spleen cells were separated to prepare single cells, which were placed on ELISPOT plate. A vehicle or αGalCer was added onto the plate, followed by culture for 6 hours for stimulation. ELISPOT assay was performed to measure the cells secreting IL-4 and IFN-γ according to the manufacturer's instruction (IL-4 ELISPOT kit, IFN-γ ELISPOT kit; R&D system).

As a result, injection of both B/αGalCer and DC/αGalCer induced high numbers of IL-4- and IFN-γ-producing cells (FIG. 2). However, it should be noted that a remarkable number of these cytokine-producing cells were detected even in the absence of αGalCer restimulation. Nevertheless, the present inventors believe the induction of IL-4- and IFN-γ-producing cells to be dependent on iNKT cells, since it did not occur in Jα 281-/-mice, which lack the iNKT population (see FIG. 2).

The present inventors intravenously administered CFSE (Carboxyfluorescein Succi nimidyl Ester) labeled B/αGalCer into naive mouse and then 24 or 48 hours after the administration the inventors analyzed the costimulatory molecules on the CFSE+ cells by flow cytometry to determine what if any changes were induced in αGalCer loaded B cells after injection. As a result, high levels of CD86 but not CD80 expression were induced within 24 hours (FIG. 3). CD40 and MHC II were also slightly upregulated. In conclusion, the in vivo administration of B/αGalCer induced the activation of B cells within 24 or 48 hours.

Next, the present inventors addressed whether co-pulsing of αGalCer and MHC I-restricted peptide on B cells could prime peptide-specific CD8+ T cells. To this end, the inventors first adoptively transferred CFSE-labeled OVA-specific CD8+ Tcells into mice, then administered vehicle-pulsed B cells (B alone), αGalCer-pulsed B cells (B/αGalCer), vehicle+peptide-pulsed B cells (B/pep), or αGalCer+peptide-pulsed B cells (B/αGalCer/pep). Then, lymphocytes were obtained from spleen and lymph nodes followed by measuring CD8+ T cell response in mice transferred with B cells. As a result, little division of OVA-specific CD8+ T cells was induced in mice receiving B alone; however a weak division of OVA-specific CD8+ T cells, probably with Ag-nonspecific origin, was noted in the B/αGalCer group. Injection of B/pep induced a substantial division of OVA-specific CD8+ T cells. And mice given B/αGalCer/pep showed an enhanced division of CD8+ T cells, with more than 40% of the resultant cells producing IL-2 and, most surprisingly, more than 90% of the resultant cells producing IFN-γ at much higher levels than the B/pep group (see FIG. 4). These results suggest that a far higher rate of CD8+ T cell activation could be achieved by the loading of αGalCer onto B/pep.

The present inventors investigated whether the B cell-based vaccine approach could induce cytotoxic immunity. Particularly, the inventors i.v. injected groups of C57BL/6 mice with B alone, B/αGalCer, B/pep, or B/αGalCer/pep and then determined in vivo CTL activity. As a result, only B/αGalCer/pep completely lysed peptide-pulsed targets (FIG. 5). And B/αGalCer/pep-treated group showed a significant increase in the number of IFN-γ-producing CD8+ T cells against the peptide (FIG. 6 left). When subsequent immunization was performed with OVA-coated syngenic splenocytes to delineate the CTL responsiveness, mice given B alone or B/αGalCer responded normally toward the priming and generated substantial peptide-specific IFN-γ-producing CD8+ T cells (FIG. 6, right). However, when splenocytes from B/pep immunized mice were restimulated with a relevant peptide in vitro, the number of IFN-γ-producing CD8+ T cells was decreased compared with those of B alone injected mice, suggesting that those mice were tolerant against the peptide. By contrast, mice vaccinated with B/αGalCer/pep acquired far greater number of peptide-reactive CD8+ T cells than did either the group receiving B/αGalCer or B alone, suggesting that this is a recall response.

The present inventors compared the efficacy of the B cell-based vaccine strategy at generating cytotoxicity with that of DC-vaccine. To this end, the inventors determined the minimum cell number required to achieve complete target cell lysis in vivo. Considering that the surface area of DC is far larger than that of B cells, B/αGalCer/pep was as efficient as DC/αGalCer/pep in generating cytotoxicity. In the meantime, the pattern of in vivo cytotoxicity of the DC/pep-treated group was very similar to that of the DC/αGalCer/pep-treated group, indicating that the loading of αGalCer onto DC did not further enhance the vaccine efficacy of DC/pep.

The present inventors next examined which types of immune cells are involved in the generation of the CTL response. To this end, the inventors injected mice with depleting Abs 4 days before or 4 days after they were vaccinated with B/αGalCer/pep and then performed an in vivo CTL assay. As a result, the generation of CTL activity was not hampered either by the depletion of CD4$^+$ or by the depletion of NK1.1+ cells regardless of depletion timing. On the other hand, CD8 depletion completely blocked the killing of target cells (FIG. 9).

It could be argued that peptide-pulsed B cells act not as APC but as reservoirs of peptide from which the host DC withdraw peptides in order to induce CTL responses. To explore this possibility, the present inventors used bm-1 mice. The cells of these mice can load OVA peptide onto their MHC class I molecules, but the resulting complex is not recognized by the cognate CD8+ T cells due to a mutation in the H-2K region. B cells from this line expressed CD1d normally and stimulated iNKT activation in response to αGalCer, indicating that the interaction between B and iNKT was intact. Again, when B/αGalCer/pep was prepared using B cells from wild-type mice and then injected into wild-type mice, complete in vivo OVA-specific cytotoxicity was generated. However, when B/αGalCer/pep derived from B cells of bm-1 mice was injected into wild-type mice, it failed to generate OVA-specific cytolytic activity, suggesting that DC or other professional APC in the recipient mice were not responsible for the CTL generation (FIG. 11).

The present inventors next examined if it were possible to generate CTL when αGalCer and peptide were pulsed separately and then injected together. As a result, mice vaccinated with 'B/αGalCer plus B/pep' failed to generate in vivo cytotoxicity (FIG. 12). This result demonstrates that peptide and αGalCer must be presented on the same B cell to generate the OVA-specific cytotoxicity.

The present inventors also investigated whether vaccination with B/αGalCer/pep would generate anti-tumor immunity. To test prophylactic anti-tumor activity, groups of mice were vaccinated once with B alone, B/αGalCer, B/pep, B/αGalCer/pep, DC/pep, or DC/αGalCer/pep before an OVA-transfected melanoma was transplanted s.c. into them. As a result, slightly delayed pattern of tumor growth was observed in mice vaccinated with B/αGalCer, though all mice finally developed tumors. In contrast, no mice receiving B/αGalCer/pep, PC/pep or DC/αGalCer/pep developed tumors (see FIG. 13). To examine whether these mice established long-term anti-tumor activity, the inventors rechallenged surviving tumor free mice with the same tumor cells 70 days after the first tumor inoculation. The inventors observed no tumor growth in those mice, demonstrating that vaccination with B/αGalCer/pep established memory immunity against the tumor (see FIG. 14).

Next, the present inventors examined whether vaccination with B/αGalCer/pep would eradicate a pre-existing tumor. As a result, tumor growth was completely repressed in mice vaccinated with DC/pep, PC/αGalCer/pep or B/αGalCer/pep (see FIG. 15 and FIG. 16).

To determine whether this B cell-based vaccine regimen can be applied to real tumor Ag, the present inventors chose the Her-2/neu model. The inventors observed a significant level of Her-2/neu-specific cytotoxicity in vivo in mice given αGalCer-loaded, Her-2/neu $_{63-71}$-pulsed B cells (see FIG. 17). To examine therapeutic anti-tumor activity in this model, the present inventors injected Her-2/neu-expressing tumor cells into mice before vaccinating them with αGalCer-loaded, Her-2/neu $_{63-71}$-pulsed B cells. After tumor inoculation, survival rates were slightly better for those mice vaccinated with B/αGalCer or B/pep than those vaccinated with B alone (see FIG. 18). In contrast, all mice vaccinated with B/αGalCer/pep survived throughout the experiment. In the solid tumor model, tumor transplanted mice were vaccinated with B cell-based vaccine or DC-based vaccine. As a result, tumor cell growth was inhibited in mice vaccinated with αGalCer-loaded, Her-2/neu $_{63-71}$-pulsed B cells as much as in mice vaccinated with DC vaccine (see FIG. 19).

Therefore, the B cell-based vaccine of the present invention proved to be as effective as DC-based vaccines in generating both prophylactic and therapeutic anti-tumor immunity.

The present invention also provides an immunotherapeutic/prophylactic vaccine and an antitumor vaccine mediated by B cells loaded with the ligand of natural killer T cells and expressing antigen.

Unlike peptide-pulsed cell vaccines, a cell vaccine transduced with viral vector to express a whole antigen can be applied to everybody without limitation in haplotypes of major histocompatibility complex and can induce the various epitopes-specific immune responses, in particular both humoral immune response and cell-mediated immune response simultaneously. B cells were transduced with adenovirus (ADHM) having a gene encoding the extracellular and transmembrane domain of Her-2/neu, a tumor-associated antigen. As a result, αGalCer presentation of B cells was not affected by transduction with AdHM (see FIG. 21). One week after immunization, lysis of target cells was not observed in mice immunized with B cells and B/αGalCer. On the contrary, a potent cytotoxic T cell immune response was observed in mice immunized with B/AdHM and B/AdHM/αGalCer (see FIG. 22 and FIG. 24).

Cytotoxic T lymphocyte response mediated by αGalCer loaded, adenovirus transduced B cells (B/AdHM/αGalCer) was continued higher and longer than that by B cells transduced with adenovirus (B/AdHM), although the difference was not significant. These results indicate that αGalCer loading on B cells, unlike peptide pulsing, does not affect the inducement of cytotoxic T cell response. However, when αGalCer loaded B cell vaccine was administered to mice, NKT cells were stimulated and thereby NK cells were activated at last in vivo, unlike in the mice administered with adenovirus transduced B cell vaccine (see FIG. 25).

To measure the efficiency of the B cell-based vaccine strategy at generating cytotoxic T lymphocyte response, the present inventors investigated the target cell lysis by vaccinating mice with a suboptimal dose which was not enough to induce complete cytotoxic T lymphocyte responses. As a result, the B cell transduced with adenovirus to express antigen could induce an antigen specific cytotoxic T lymphocyte response effectively, even though high number of B cells was required, compared with peptide-pulsed B cell vaccine. Since approximately 20% of the total B cells transduced with adenovirus actually expressed Her-2/neu, the efficacy of B cells transduced with adenovirus has been forced to be underestimated in effect. In case of transferring a small number of B cells, NKT cell activation induced by αGalCer loaded B cells was helpful for the target cell lysis induced by adenovirus transduced B cells.

A virus which infects B cells to express a tumor antigen can be exemplified by adenovirus, retrovirus, vaccinia virus, pox virus and sindbis virus, but not always limited thereto. In addition to using a viral vector, following methods can be used to transfer an gene encoding antigen; 1) binding DNA to liposome to protect the DNA from being decomposed by an enzyme or to be absorbed into endosome; 2) binding DNA to a molecular conjugate or a synthetic ligand to increase transfection efficacy (ex: Asialoglycoprotein, transferrin and polymeric IgA); 3) constructing a new DNA transduction system using PTD (protein transduction domain) to increase transduction efficiency of gene encoding antigen (ex: Mph-1); and 4) introducing peptide or protein to B cells to present the antigen.

The present invention further provides a natural killer T cell activator mediated by αGalCer loaded B cells.

As explained hereinbefore, αGalCer-loaded B cells of the present invention, like αGalCer-loaded dendritic cells, stimulate natural killer T cell hybridoma in vitro and thus induce the secretion of IL-2 (see FIG. 30) and effectively activate iNKT cells which could induce the activation of various immune cells in vivo (see FIG. 2). Therefore, αGalCer loaded B cells of the present invention can be used as a natural killer T cell activator just as αGalCer loaded dendritic cells can be.

The present invention also provides a cytotoxic response inducer mediated by tumor antigen expressing B cells.

Unlike the B cell vaccine pulsed with a peptide to induce cell-mediated immune response, the B cell vaccine transduced with adenovirus can induce both cell-mediated immune response and humoral immune response simultaneously. To confirm whether the B cell vaccine transduced with AdHM could induce Her-2/neu specific antibody, mice were immunized with B/AdHM and B/AdHM/αGalCer, respectively, and then anti-Her-2/neu antibody titer in sera was measured. As a result, anti-Her-2/neu antibody titer was maintained high for a long while in both groups immunized with B/AdHM and B/AdHM/αGalCer (see FIG. 27). Unlike the groups immunized with B cells alone (B) and B/αGalCer, the humoral immune response was generated in both groups immunized with B/AdHM and B/AdHM/αGalCer (see FIG. 28).

One week after immunization with the B cell-based vaccine, the present inventors performed intravenous injection of Her-2/neu expressing murine tumor cells (TAUF), followed by investigation of survival rate. As a result, mice administered with either αGalCer loaded B cells (B/αGalCer) or AdHM transduced B cells (B/AdHM) survived longer than those administered with B cells alone. Furthermore, antitumor effect of mice administered with the B cells transduced with adenovirus express Her-2/neu and loaded with αGalCer was more significant than that of B/AdHM immunized mice (see FIG. 29). Therefore, it was confirmed that αGalCer loaded and adenovirus transduced B cell vaccine can effectively induce immune responses to prevent tumor.

To confirm the therapeutic effect of the B cell vaccine, BALB/c mice were immunized with B, B/αGalCer, B/AdHM and B/AdHM/αGalCer, respectively, following intravenous injection of TAUF to the tail vein to establish lung cancer. As a result, the shortest survival time was observed in the mouse group treated with B cells only, and the result of the group treated with B/αGalCer vaccine was similarly short. In the meantime, the survival time was more or less prolonged in the mouse group treated with B/AdHM vaccine, compared with the groups treated with B or B/αGalCer, but tumor formation was not inhibited completely. But the survival time was much longer in the group treated with B/AdHM/αGalCer, compared with all the other groups, and thus antitumor effect of B/AdHM/αGalCer group was greater than any other immunized groups (see FIG. 29).

The vaccine of the present invention can additionally include, in addition to the natural killer T cell ligand and B cells, one or more effective ingredients having the same or similar effect with them. The vaccine can also include, in addition to the above-mentioned effective ingredients, one or more pharmaceutically acceptable carriers for the administration. The pharmaceutically acceptable carrier can be selected or be prepared by mixing more than one ingredients selected from a group consisting of saline, sterilized water, Ringer's solution, buffered saline, dextrose solution, maltodextrose solution, glycerol and ethanol. Other general additives such as anti-oxidative agent, buffer solution, bacteriostatic agent, etc., can be added. In order to prepare injectable solutions such as aqueous solution, suspension and emulsion, diluents, dispersing agents, surfactants, binders and lubricants can be additionally added. The vaccine of the present invention can further be prepared in suitable forms for each disease or according to ingredients by following a method represented in Remington's Pharmaceutical Science (the newest edition), Mack Publishing Company, Easton Pa.

The vaccine of the present invention can be administered by parenterally and the parenteral administration includes subcutaneous injection, intravenous injection, intramuscular injection and intrathoracic injection. To prepare the vaccine as a formulation for parenteral administration, B cells loaded with the natural killer T cell ligand, B cells loaded with the natural killer T cell ligand and a peptide or B cells transduced with a virus expressing a tumor antigen is mixed with a stabilizer or a buffering agent to produce a solution or suspension, which is then formulated as ampoules or vials (see the standard for the production of a virus vector used for the transduction of dendritic cells).

The vaccine can be administered by effective dose to induce immune response in a patient. For example, the vaccine can be administered to human once or a few times a day by the dosage of $1\times10^3 \sim 1\times10^9$ cells/kg, and more preferably $1\times10^4$ cells/kg~$1\times10^8$ cells/kg. To prepare αGalCer loaded B cell vaccine, a medium has to be supplemented with αGalCer at the concentration of 1~2 μg/ml per $1\times10^6 \sim 1\times10^7$ B cells/ml. To prepare αGalCer and peptide co-pulsed B cell vaccine, a medium has to be supplemented with αGalCer at the concentration of 1~2 μg/ml per $1\times10^6 \sim 1\times10^7$ B cells/ml and peptide at the concentration of 1~10 μg/ml per $1\times10^6 \sim 1\times10^7$ B cells/ml.

αGalCer doesn't seem to induce toxicity in rodents and apes (Nakata et al., Cancer Res., 58: 1202-1207, 1998). No side effects have been reported when 2200 μg/kg of αGalCer was administered into a mouse (Giaccone et al., Clin. Cancer Res., 8: 3702, 2002). From the clinical trial, a light headache has been reported as a side effect according to the systemic administration of αGalCer (Mie Nieda et al., Blood, 103: 383-389, 2004, Giaccone et al., Clin. Cancer Res., 8: 3702, 2002), which can be prevented by the administration of paracetamol. There is a little, if ever, chance to show a slight systemic side effect (Giaccone et al., Clin. Cancer Res., 8: 3702, 2002). In the present invention, αGalCer did not cause dose-limiting toxicity (50-4800 μmg/$^2$) and showed resistance through dose escalation study, indicating that αGalCer is a very safe substance.

The peptide herein includes virus, bacteria, fungi, parasites and tumor originated antigen peptide and the introduced antigen to B cells mediated by viral vector includes virus, bacteria, fungi, parasites and tumor-originated antigen.

An "antigen" means every substance (ex, protein, peptide, tumor cells, glycoprotein, glycolipid, live virus, killed virus, DNA etc.) that is able to induce immune response by being recognized by the immune system when it invades into a host. The antigen can be prepared as a purified or non-purified form but a purified form is preferred. The antigen of the present invention includes protein of pathogen, recombinant protein, peptide, polysaccharide, glycoprotein, lipopolysaccharide and DNA molecule (polynucleotide), tumor cells, live virus and killed virus.

Antigens presented in the below antigen list can be provided as a tool to induce immune response instead of the tumor-associated antigen of Examples of the invention, but not always limited thereto. The list includes influenza virus antigen (haemagglutinin and neuraminidase antigens), *Bordetella pertussis* antigen (pertussis toxin, filamentous haemagglutinin and pertactin), human papilloma virus (HPV) antigen (glycoprotein), *Helicobacterpylori* antigen (capsula polysaccharides of serogrup A, B, C, Y and W-135), tetanus toxoid, diphtheria antigen (diphtheria toxoid), pneumococcal antigen (*Streptococcus pnemoniae* type 3 capsular polysaccharide), tuberculosis antigen, human immunodeficiency virus (HIV) antigen (GP-120, GP-160, p18, Tat, Gag, Pol and Env), cholera antigen (cholera toxin B subunit), staphylococcal antigen (staphylococcal enterotoxin B), *shigella* antigen (*shigella* polysaccharides), vesicular stomatitis virus antigen (vesicular stomatitis virus glycoprotein), cytomegalovirus (CMV) antigen, hepatitis antigen (hepatitis A(HAV), B(HBV), C(HCV), D(HDV) and G(HGV) antigens) (core antigen and surface antigens), respiratory synctytial virus (RSV) antigen, herpes simplex antigen or their combinations (ex, diphtheria, pertussis and tetanus, DPT), *Borrelia* sp. antigen (ex, OspA, OspB and OspC antigens), *Candida albicans* antigen (ex, MP65), and Plasmodium antigen (ex, CS protein).

A tumor antigen is generated by the somatic mutation of a wild type gene. The cancer antigen includes a tumor-specific antigen attributed to the genetic instability of a tumor cell and a tumor-associated antigen, an endogenous autoantigen, which is expressed more in tumor cells and temporarily expressed in tumor development stage or expressed in specific tissue restrictedly. A tumor specific antigen is exemplified by HPV E6/E7 which is a cancer virus originated antigen, and a tumor-associated antigen is exemplified by gp100, tyrosinase, TRP-1 (tyrosinase-related protein-1), TRP-2 (tyrosinase-related protein-2), MAGE, MUC-1, CEA (carcinoembryonic antigen), p53, alpha-fetoprotein and Her-2/neu, etc (Rosenberg S A., Nature, 17; 411(6835):380-4, 2001).

BRIEF DESCRIPTION OF THE DRAWINGS

The application of the preferred embodiments of the present invention is best understood with reference to the accompanying drawings, wherein:

FIG. 1-FIG. 3 are graphs illustrating the reciprocal activation between iNKT cells and αGalCer-loaded B cells, FIG. 1 is a set of graphs illustrating that B cells were purified from spleen after depletion of CD11c$^+$ cells, followed by measuring the expressions of CD19, CD11c and CD1d by flow cytometry.

FIG. 2 is a set of graphs illustrating that C57BL/6 wildtype or J 281$^{-/-}$ mice were iv injected with the vehicle alone, with a free form of αGalCer, or with αGalCer-loaded B cells (B/αGalCer) or DC (DC/αGalCer), and then splenocytes from the recipient mice were obtained and IL-4- and IFN-γ-producing cells were analyzed by ELISPOT assay, FIG. 3 is a set of graphs illustrating that vehicle- or αGalCer-loaded B cells were stained with CFSE and injected into C57BL/6 mice. CFSE$^+$ cells from splenocytes were analyzed, FIG. 4-FIG. 6 are graphs showing that B cells co-pulsed with αGalCer and peptide (OVA$_{257-264}$) activate the peptide specific CD8+ T cells, FIG. 4 is a set of graphs illustrating that CFSE labeled OVA$_{257-264}$ specific CD8+ T cells (OT-1 T cells) were transferred into C57BL/6 mice, to which B/vehicle, B/αGalCer, B/pep or B/αGalCer/pep was respectively administered. Then, OT-1 T cell proliferation and cytokine secretion were investigated by flow cytometry, FIG. 5 is a set of graphs illustrating that C57BL/6 mice were vaccinated with the indicated forms of B cells (B alone, B/αGalCer, B/pep or B/αGalCer/pep). One, three or five weeks later, in vivo CTL assays were performed by injecting CFSE-labeled syngenic targets, CFSE$^{high}$: peptide-pulsed target, CFSE$^{low}$: peptide-unpulsed control FIG. 6 is a set of graphs illustrating that the response by IFN-γ-producing CD8+ T cells to OVA$_{257-264}$ restimulation in vitro was calculated 7 days after the administration of B cell-based vaccines (left) or 7 days after additional CTL priming with OVA$_{257-264}$-loaded syngenic splenocytes (right), FIG. 7 and FIG. 8 are graphs comparing the efficiency in cytotoxic T lymphocyte generation between B cell-based and DC-based cellular vaccine, FIG. 7 is a set of graphs illustrating that OVA$_{257-264}$ peptide pulsed B/αGalCer/pep and DC/αGalCer/pep were serially diluted, which were then administered into mice, and then in vivo cytotoxicity against OVA$_{257-264}$ was measured, FIG. 8 is a set of graphs illustrating that OVA$_{257-264}$ pulsed B/vehicle/pep and DC/vehicle/pep were administered by the same manner as described in FIG. 7, and then in vivo cytotoxicity against OVA$_{257-264}$ was measured, FIG. 9 and FIG. 10 are graphs showing the types of immune cells involved in CTL response induced by the B cell-based vaccine, FIG. 9 is a set of graphs illustrating that B cells co-pulsed with αGalCer and OVA$_{257-264}$ were injected into mice. The recipient mice received immune cell depleting mAbs, then tested for in vivo cytotoxicity against OVA$_{257-264}$.

FIG. 10 is a graph illustrating that B cells co-pulsed with αGalCer and OVA$_{257-264}$ peptide were injected into wild type, Jα281$^{-/-}$ or MHC class II$^{-/-}$ mice, followed by standard $^{51}$Cr release assay to investigate in vitro cytotoxicity against OVA$_{257-264}$, FIG. 11 and FIG. 12 are graphs showing that B cells co-pulsed with αGalCer and OVA$_{257-264}$ peptide act as direct antigen-presenting cells for CD8+ T cells, FIG. 11 is a set of graphs illustrating that B cells from wild-type mice or bm-1 mice were co-pulsed with αGalCer and OVA$_{257-264}$ before being injected into wild-type mice, then, in vivo cytotoxicity against OVA$_{257-264}$ was measured, FIG. 12 is a set of graphs illustrating that C57BL/6 mice were vaccinated with B cells co-pulsed with αGalCer and OVA$_{257-264}$ or 'a combination of B cells pulsed with OVA$_{257-264}$ and of B cells pulsed with αGalCer', then, in vivo cytotoxicity against OVA$_{257-264}$ was measured, FIG. 13-FIG. 16 are graphs illustrating that the B cell-based vaccine can offer both prophylactic and therapeutic anti-tumor immunity against OVA-transfected B16 melanoma, FIG. 13 is a graph illustrating that C57BL/6 mice were vaccinated with the indicated cellular vaccine (B alone, B/αGalCer, B/pep, B/αGalCer/pep, DC/pep or DC/αGalCer/pep). Seven days later, MO-5 tumor cells were subcutaneously injected into the mice and then tumor mass was measured, FIG. 14 is a graph illustrating that the growth of rechallenged tumor cells was inhibited in tumor-free mice shown in FIG. 13. Seventy days after the first tumor inoculation, tumor-free mice were rechallenged subcutaneously with MO-5 cells (2×10$^5$) and tumor mass was measured, FIG. 15 and FIG. 16 are graphs illustrating that C57BL/6 mice were vaccinated with the indicated cellular vaccine (B alone, B/αGalCer, B/pep, B/αGalCer/pep, DC/pep or DC/αGalCer/pep). One day or nine days later, MO-5 tumor cells were subcutaneously injected into the mice and then tumor mass was measured,

*, p<0.05 in comparison with 'B alone' control group (FIG. 13, FIG. 15 and FIG. 16) or with age-matched naive mice (FIG. 14).

FIG. 17-FIG. 19 are graphs illustrating that the B cell-based vaccine triggers therapeutic anti-tumor immunity against Her-2/neu-expressing tumor, FIG. 17 is a set of graphs illustrating that BALB/c mice were vaccinated with B cells or DC after coculture with αGalCer or vehicle plus Her-2/neu$_{63-71}$(hP63) as indicated, and then in vivo CTL assays were performed, FIG. 18 and FIG. 19 are graphs illustrating that BALB/c mice were challenged i.v. (FIG. 18) or s.c. (FIG. 19) with CT26-Her2/neu by the same manner as described in the above, followed by immunizing the mice with B cells or DCs and the survival rates (FIG. 18) or tumor growth (FIG. 19) of these mice was measured, FIG. 20 and FIG. 21 are graphs illustrating the trial to test if the way of transduction of B cells with an entire antigen using a viral vector can be applied to the B cell vaccine or not, FIG. 20 is a set of graphs illustrating that B cells were infected with the adenovirus (AdHM) expressing the extracellular domain and the transmembrane domain of Her-2/neu, a tumor-associated antigen, and then Her-2/neu expression on the surface of B cell was measured, FIG. 21 is a graph illustrating that AdHM-transduced and αGalCer-loaded B cells could activate DN32.D3 cells. Particularly, DN32.D3 cells were cultured respectively with B cells alone, αGalCer-loaded B cells, AdHM-transduced B cells, and AdHM-transduced and αGalCer-loaded B cells and then the level of IL-2 in each supernatant was measured by ELISA, FIG. 22-FIG. 24 are graphs illustrating that B cells transduced with the tumor-associated antigen Her-2/neu induce cytotoxic immune response effectively, FIG. 22 is a graph illustrating that mice were immunized respectively with B cells isolated from the spleen of BALB/c mice and then transduced with the adenovirus (B/AdHM), B cells additionally loaded with αGalCer (B/AdHM/αGalCer), B cells only, and B cells loaded with αGalCer (B/αGalCer). Each mouse was transferred with target cells loaded with cytotoxic T cell epitope to investigate antigen specific cytotoxic T lymphocyte response in vivo, FIG. 23 is a graph comparing the durations of cytotoxic T cell response in each mouse group immunized with B/AdHM and B/AdHM/αGalCer, FIG. 24 is a graph comparing the levels of IFN-γ secreted by CD8+ T cells before and after stimulating each mouse immunized with B/AdHM and B/AdHM/αGalCer with cytotoxic T cell peptide in vitro, naive: a mouse group not treated with vaccine FIG. 25 and FIG. 26 are graphs illustrating that adenovirus-transduced B cell vaccines (B/AdHM/αGalCer) could effectively activate natural killer cells and induce cytotoxic T cell response, FIG. 25 is a graph showing the activation of natural killer cells, FIG. 26 is a graph showing the target cell lysis depending on the dose of cell vaccine, which was investigated to compare the efficiency in inducing cytotoxic T cells, FIG. 27 and FIG. 28 are graphs illustrating that the B cell vaccine transduced with AdHM (B/AdHM and B/AdHM/ αGalCer) could induce Her-2/neu specific antibody, FIG. 27 is a graph illustrating that BALB/c mice were immunized with B/AdHM and B/AdHM/αGalCer respectively, and then anti-Her-2/neu antibody titer was measured to investigate the binding of anti-Her-2/neu antibody in serum to the murine tumor cell expressing Her-2/neu on its surface (TAUF), FIG. 28 is a graph showing the humoral immune response of each group, FIG. 29 is a set of graphs showing the antitumor activity of the B cell vaccine transduced with the adenovirus. Particularly, lung cancer was induced in a mouse by inoculating with TAUF, followed by immunization with the B cell vaccine, FIG. 30 is a set of graphs illustrating the secretion of IL-2, which is an index for the activation of natural killer T cells, by the activation of natural killer T cells induced by αGalCer-loaded B cells, according to the concentration of αGalCer, and the activation of natural killer T cells induced by αGalCer-loaded B cells or DC according to the cell concentration, FIG. 31-FIG. 35 are graphs illustrating that specific immune cells could be eliminated by the administration of an antibody that is able to deplete CD4+, CD8+ or NK1.1 cell in vivo, FIG. 36 is a graph showing the antitumor immune activity against thymoma (EG-7) induced by the B cell-based vaccine.

*,p<0.001: statistic significance, compared with a group treated with B cells only.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Bidirectional Activation of αGalCer-Loaded B cells and iNKT Cells

<1-1> Comparison of iNKT Cell Activation Induced by B Cells and that Induced by DC Since it was already well established that αGalCer-loaded DC activate iNKT cells (Kim, S., et al., Synthesis, 847, 2004), the present inventors investigated whether αGalCer-loaded B cells have similar effect with the αGalCer-loaded DC or not.

Female C57BL/6 and BALB/c mice were used at the age of 6-10 weeks. The OT-I and C57BL/6$^{bm1}$ (bm1) mice were purchased from The Jackson Laboratory, while J 281$^{-/-}$ mice and MHC II$^{-/-}$ mice were kindly provided by Dr. Chung (Seoul National University, Korea) (Kim J H et al., Am J Pathol., 167(5):1231-41, 2005) and Dr. Park (Korea University, Korea) (Park, S. H., et al., J. Exp. Med. 193:893, 2001) respectively. All mice were kept under specific pathogen-free conditions in the Animal Center for Pharmaceutical Research at Seoul National University, Korea. Antibodies from hybridomas, namely GK1.5 (anti-CD4: ATCC number: TIB-207), 2.43 (anti-CD8; ATCC number: TIB-210), and PK136 (anti-NK1.1; ATCC number: HB-191) were obtained and injected i.p. (150 µg/mouse) to deplete the respective lymphocyte subsets in vivo.

Particularly, to separate B cells from each mouse, the spleen was isolated from a mouse, followed by homogenization. After depleting CD11c$^+$ cells from the spleen by anti-CD11c microbeads (Miltenyibiotec), the present inventors isolated pure B cells using anti-B220 microbeads (Miltenyibiotec). These cells were >99% CD19-positive (see FIG. 1).

To separate dendritic cells from the spleen, the spleen taken out from a mouse was placed in a 7 ml medium containing collagenase D (1 mg/ml, Roche) and DNase I (50 μg/ml, Sigma-Aldrich), followed by reaction at 37° C. for 30 minutes. EDTA was added (final conc. 10 mM, pH 7.2) to the medium, followed by further reaction for 5 more minutes. Dendritic cells were separated from the splenocytes by 15.5% Accudenz density gradient (Accurate Chemical & Scientific).

Purified cells (B cells or DC) were cocultured with αGalCer (1 μg/ml) or the vehicle (0.5% polysorbate) for 14 hr in a $CO_2$ incubator. Then, the cells were cocultured with a natural killer T cell hybridoma, DN32.D3 (Claire Forestier et al., The Journal of Immunology, 171: 4096, 2003); IL-2 was then measured as an indicator of NKT activation by sandwich ELISA.

As a result, αGalCer-loaded DC (DC/αGalCer) stimulated DN32.D3 to produce IL-2. Similarly, αGalCer-loaded B cells (B/αGalCer) efficiently stimulated DN32.D3 cells to produce IL-2, equaling the DC group's rate of IL-2 production when at higher ratios to the hybridoma but falling short when at lower ratios (see FIG. 30).

<1-2> Activation of Natural Killer T Cell Dependent Immune Response

To investigate whether B/αGalCer and DC/αGalCer administered in vivo could activate immune cells or not, the present inventors injected B/αGalCer or DC/αGalCer from C57BL/6 mice i.v. into syngenic mice and measured the level of IL-4- and IFNγ-producing cells by ELISPOT. Particularly, wild type C57BL/6 or Jα281-/-mice were intravenously injected with vehicle, αGalCer, αGalCer-loaded B cells or αGalCer-loaded DC. One week later, spleen was separated to prepare single cells, which were placed on ELISPOT plate. A vehicle or αGalCer was added onto the plate, followed by culture for 6 hours for stimulation. ELISPOT was performed to measure the cells secreting IL-4 and IFN-γ according to the manufacturer's instruction (IL-4 ELISPOT kit, IFN-γ ELISPOT kit; R&D system).

As a result, injection of both B/αGalCer and DC/αGalCer induced high numbers of IL-4- and IFN-γ-producing cells (FIG. 2). However, it should be noted that a remarkable number of these cytokine-producing cells were detected even in the absence of αGalCer restimulation. Nevertheless, the present inventors believe the induction of IL-4- and IFN-γ-producing cells to be dependent on iNKT cells, since it did not occur in J 281-/-mice, which lack the iNKT population (see FIG. 2).

<1-3> B Cell Activation by Natural Killer T Cell Activation

To determine what if any changes were induced in B cells after injection, the present inventors intravenously administered CFSE (Carboxyfluorescein Succinimidyl Ester) labeled B/αGalCer and then analyzed the costimulatory molecules on the CFSE+ cells. Particularly, lymphocytes were obtained from the spleen and lymph node of C57BL/6 mice and CD11c+ cells were eliminated by using anti-CD11c microbeads (Miltenyibiotec). B cells were separated by using anti-B220 microbeads (Miltenyibiotec). The separated B cells were labeled with 10 μM of CFSE, which were injected into the tail vein of a syngeneic mouse. To label with CFSE, CFSE (Molecular Probe) was diluted in RPMI medium at proper concentration, followed by reaction at 37° C. for 15 minutes for labeling. The cells were washed with RPMI medium three times to eliminate remaining CFSE. Twenty four and forty eight hours after labeling, costimulatory molecules in CFSE+ cells separated from the spleen and lymph node of the mouse were investigated by flow cytometry.

As a result, high levels of CD86 but not CD80 expression were induced within 24 hr. CD40 and MHC II were also slightly upregulated (FIG. 3). Even 48 hr after injection, no upregulation of CD80 was observed and all other results remained largely consistent with the 24-hr level. That is, B cells were activated by the natural killer T cells activated by B/αGalCer within 24 hours.

Considering the results of Examples <1-1>, <1-2> and <1-3>, it was confirmed that both DC/αGalCer and B/αGalCer are capable of fully activating iNKT cells both in vitro and in vivo, and the activation is bi-directional in vivo (since both iNKT and B cells were activated).

Example 2

Peptide-Pulsed B/αGalCer Promotes the Activation of Peptide-Specific CD8+ T Cells The present inventors examined whether co-pulsing of αGalCer and MHC I-restricted peptide on B cells could prime peptide-specific CD8+ T cells. To this end, the inventors first adoptively transferred CFSE-labeled OVA-specific CD8+ T cells (OT-I) into C57BL/6 mice, then administered vehicle-pulsed B cells (B alone), B/αGalCer, vehicle and $OVA_{257-264}$ peptide-pulsed B cells (B/pep), or αGalCer and $OVA_{257-264}$ peptide-pulsed B cells (B/αGalCer/pep). Forty eight hours later, single cells were obtained from the spleen, and then OT-I cell proliferation was observed. In the meantime, OT-I cells secreting IL-2 and IFN-γ were cultured with 1 μM of $OVA_{257-264}$ peptide and 1 μL/mL of GolgiPlug for four hours, and then intracellular cytokine staining was performed using Cytoperm/Cytofix kit (BD Pharmingen).

As a result, little division of OVA-specific CD8+ T cells (OT-I cells) was induced in mice receiving B alone; however a weak division of OVA-specific CD8 T cells, in a Ag-non-specific manner, was noted in the B/αGalCer group (FIG. 7, 1.2±0.5% vs 5.4±1.8%). Injection of B/pep induced a substantial division of OT-I, but very few of these cells produced IL-2 (<4%) and relatively few produced IFN-γ (38%) after restimulation in vitro. By contrast, mice given B/αGalCer/pep showed an enhanced division of OT-I, with more than 40% of the resultant cells producing IL-2 and, most surprisingly, more than 90% producing IFN-γ at much higher levels than the B/pep group (FIG. 4).

These results suggest that a far higher rate of CD8+ T cell activation could be achieved by the loading of αGalCer onto B/pep.

Example 3

Long-Lasting Cytotoxic T Cell Response and Overcome of Immune Tolerance by B/αGalCer/pep <3-1> Long-Lasting Cytotoxic T Cell Response Induced by B/αGalCer/pep The present inventors investigated whether the B cell-based vaccine approach could induce cytotoxic immunity. To this end, the inventors injected i.v. groups of C57BL/6 mice with B alone, B/αGalCer, B/pep, or B/αGalCer/pep and then determined in vivo CTL activity. In addition, the inventors investigated if the cytotoxic immune response induced by the B cell-based vaccine could be continued. Particularly, C57BL/6 mice were immunized with B alone, B/αGalCer, B/pep and B/αGalCer/pep respectively. At the first, third and fifth week of immunization, in vivo CTL assay was performed. Syngenic lymphocytes were either loaded with $OVA_{257-254}$ peptide or left untouched before being labeled with 20 μM ($CFSE^{high}$) or 2 μM ($CFSE^{low}$) of CFSE. Equal numbers of the two populations were mixed and injected i.v.

into mice. Next day, the single cells were obtained and CFSE$^{high}$ and CFSE$^{low}$ were measured by flow cytometry. The lower number of CFSE$^{high}$ means the higher the cytotoxic immune response.

As a result, only B/αGalCer/pep completely lysed peptide-pulsed targets, and it also maintained complete cytotoxicity even 5 weeks after a single injection. In the meantime, neither B/pep nor B/αGalCer induced any peptide-specific CTL responses in mice. Only the B/αGalCer/pep-treated group showed a significant increase in the number of IFN-γ-producing CD8+ T cells against OVA$_{257-264}$ (FIG. 6, left).

<3-2> Confirmation of the Overcome of Immune Tolerance by B/αGalCer/pep

In general, the administration of an antigen alone induces immune tolerance. Thus, the present inventors investigated whether the immune tolerance induced by an antigen could be overcome or not when αGalCer was loaded together with a peptide on B cells. Particularly, C57BL/6 mice were immunized by the same manner as described in Example <3-1>. One week later, splenocytes were obtained, followed by stimulation with OVA-coated syngenic splenocytes for one week. CD8+ T cells secreting IFN-γ in the stimulated splenocytes were measured by the intracellular cytokine staining.

As a result, mice given B alone or B/αGalCer responded normally toward the priming and generated substantial peptide-specific IFN-γ-producing CD8+ T cells (FIG. 6, right). However, mice given B/pep showed no increase in the number of IFN-γ-producing CD8+ T cells, suggesting that these mice were tolerant of the peptide.

By contrast, mice vaccinated with B/αGalCer/pep acquired far greater number of peptide-reactive CD8+ T cells than did either the group given B alone or B/αGalCer. At this time, the mice vaccinated with B alone or B/αGalCer were not administered with any antigen, so the antigen specific immune response was not induced in the mice and the in vitro stimulation with OVA-coated splenocytes was the first and the only stimulation causing immune response. However, the mice vaccinated with B/αGalCer/pep had already been administered with an antigen, so the in vitro stimulation with OVA-coated splenocytes was recall response. In conclusion, B/αGalCer/pep overcomes immune tolerance, showing immunogenicity and strong recall response.

Example 4

B Cell-Based Vaccine is as Efficient a Generator of CTL as DC-Based Vaccine

The present inventors compared the efficacy of the B cell-based vaccine at generating cytotoxicity with that of DC-vaccine.

To this end, the inventors determined the minimum cell number required to achieve complete target lysis in vivo. Particularly, B cells or DC were cocultured with αGalCer or vehicle for 16-18 hours and then pulsed with 1 μg/ml of OVA$_{257-264}$ for an hour. Serially diluted cells were i.v. injected into syngenic mice and an in vivo CTL assay was performed. As explained in the above Example, peptide-pulsed targets were labeled as CFSE$^{high}$ and control cells not pulsed with a peptide were labeled as CFSE$^{low}$. Equal numbers of the two populations were mixed and injected i.v. into mice. After a while, the splenocytes of the mice were examined by flow cytometry to calculate the ratio of CFSE$^{low}$:CFSE$^{high}$ to measure the antigen specific target cell lysis.

As a result, mice injected with DC/αGalCer/pep showed a complete target cell lysis with as few as 16,000 cells. Of interest, a single vaccination with 80,000 B/αGalCer/pep cells was enough to establish a complete peptide-specific lysis, while vaccination with 16,000 cells generated a moderate cytotoxicity (FIG. 7). However, given that the surface area of DC is far larger than that of B cells, B/αGalCer/pep can be said to be as efficient as DC/αGalCer/pep in generating cytotoxicity. DC/pep efficiently generated OVA-specific cytotoxicity while B/pep-treatment, regardless of the number of cells tested, did not (FIG. 8). Of note, the pattern of in vivo cytotoxicity of the DC/pep-treated group was very similar to that of the DC/αGalCer/pep-treated group, indicating that the loading of αGalCer onto DC did not enhance the vaccine efficacy of DC/pep.

Example 5

Requirement of the Generation of CTL by B/αGalCer/pep

The present inventors examined which type of immune cells are involved in the generation of the CTL response. To this end, the inventors injected mice with depleting Abs (anti-CD4 depleting antibody: GK1.5, anti-CD8 depleting antibody; 2.43, anti-NK1.1 depleting antibody; PK136). Four days before or four days after they were vaccinated with B/αGalCer/pep and then performed an in vivo CTL assay.

As a result, the timing of depletion made no difference, as the generation of CTL activity was not hampered in either case by the depletion of CD4$^+$ or NK1.1$^+$ cells (FIG. 9). On the contrary, CD8 depletion completely blocked the killing of target cells. Consistent with these results, MHC II$^{-/-}$ mice (lacking CD4+ T cells) developed normal CTL responses, while Jα281$^{-/-}$ mice (lacking iNKT cells) failed to do so (FIG. 10).

Example 6

Antigen-Presenting and Cytotoxic T Lymphocyte Inducement by B Cells

It could be argued that peptide-pulsed B cells act not as APC but as reservoirs of peptide from which the host DC withdraw peptides in order to induce CTL responses. To explore this possibility, the present inventors used bm-1 mice (Norbury, C. C. et al., Science 304, 1318-1321, 2004). The cells of these mice can load OVA peptide onto their MHC I, but the resulting complex is not recognized by the cognate CD8+ T cells due to a mutation in the H-2K region. B cells from this line expressed CD1d normally and stimulated iNKT activation in response to αGalCer, indicating that the interaction between B and iNKT was intact.

Again, when B/αGalCer/pep was prepared using B cells from wild-type mice and then injected into wild-type mice, complete in vivo OVA-specific cytotoxicity was generated. However, when B/αGalCer/pep derived from B cells of bm-1 mice was injected into wild-type mice, it failed to generate OVA-specific cytolytic activity, suggesting that DC or other professional APC in the recipient mice were not responsible for the CTL generation (FIG. 11).

The present inventors investigated if it were possible to generate CTL when αGalCer and peptide were pulsed separately and then injected together. To this end, C57BL/6 mice were i.v. injected with 'B/αGalCer plus B/pep' or B/αGalCer/pep alone and in vivo CTL assay was performed.

As a result, mice, vaccinated with 'B/αGalCer plus B/pep' failed to generate in vivo cytotoxicity (FIG. 12). This result demonstrates that peptide and αGalCer must be presented on the same B cell to generate the cytotoxicity.

Example 7

Antitumor Effect of B/αGalCer/pep

<7-1> In vivo Test Using OVA Models

The present inventors examined whether vaccination with B/αGalCer/pep could generate anti-tumor immunity. To test prophylactic anti-tumor activity, groups of mice were vaccinated once with B alone, B/αGalCer, B/pep, B/αGalCer/pep, DC/pep, or DC/αGalCer/pep before an OVA-transfected B16 melanoma (MO-5) (Dr. Kenneth Rock, University of Massachusetts: Falo, L. D., et al., Nat. Med. 1: 649, 1995) was transplanted s.c. into them. As a result, a slightly delayed pattern of tumor growth in mice vaccinated with B/αGalCer was observed, though all mice finally developed tumors (FIG. 13). In contrast, no mice receiving B/αGalCer/pep, DC/pep or DC/αGalCer/pep developed tumor growth.

To examine whether these mice established long-term anti-tumor activity, the inventors rechallenged surviving mice with MO-5 tumors 70 days after the first tumor inoculation. As a result, the inventors observed no tumor growth in those mice (FIG. 14), demonstrating that vaccination with B/αGalCer/pep established memory immunity against the tumor. When the inventors performed similar experiments using a tumor of different origin, OVA-transfected thymoma (EG-7), very similar and consistent results were obtained (FIG. 36).

The present inventors investigated whether vaccination with B/αGalCer/pep could eradicate a pre-existing tumor. To this end, the inventors established two therapeutic models; mice were vaccinated (i) one day or (ii) nine days after s.c. transplant, when tumors had become palpable.

In the one-day model, vaccination with either DC/pep or DC/αGalCer/pep almost completely suppressed tumor growth. Interestingly, tumor growth was also completely diminished in mice vaccinated with B/αGalCer/pep (FIG. 15). In the nine-day model, none of these vaccinations completely destroyed the growing tumor, due to the very aggressive nature of the B16 melanoma. However, in mice vaccinated with B/αGalCer/pep, tumor growth was less pronounced than in 'B-alone' group of mice and resembled that observed in the DC/pep- or DC/αGalCer/pep-vaccinated groups (FIG. 16).

<7-2> In vivo Test Using Her-2/neu Models

To investigate whether the B cell-based vaccine could be applied to real tumor Ag, experiments were performed using TAUF (Penichet M L et al., Lab Anim Sci., 49: 179-88, 1999), a tumor cell line expressing Her-2/neu by the same manner as described in the above Example <7-1>. This tumor Ag is well characterized and its CTL epitope is known. Again, the inventors observed a significant level of Her-2/neu-specific cytotoxicity in vivo in mice given αGalCer-loaded Her-2/neu$_{63-71}$-pulsed B cells (FIG. 17).

To examine anti-tumor activity in this model, the present inventors injected Her-2/neu-expressing tumor cells (TAUF) i.v. or s.c. into BALB/c mice before vaccinating them with Her-2/neu$_{63-71}$-pulsed αGalCer-loaded B cells. After i.v. tumor inoculation, survival rates were slightly better for those mice vaccinated with B/αGalCer or B/pep than those vaccinated with B alone (FIG. 18). In contrast, all mice vaccinated with B/αGalCer/pep survived throughout the experiment. These surviving mice also resisted rechallenge with TAUF. Similar results were observed in the s.c. tumor growth model (FIG. 19).

Collectively, the B cell-based vaccine regimen proved to be as effective as DC-based vaccines in generating both prophylactic and therapeutic anti-tumor immunity.

Example 8

Introduction of the Whole Antigen Using Antigen-Expressing Virus Vector

A peptide-pulsed cell vaccine cannot be generally used because the application of the peptide is limited to haplotypes of major histocompatibility complex (MHC) and can only present a single epitope. On the other hand, a virus mediated entire antigen can be widely used without limitation in haplotypes of MHC and can induce both humoral immune response and cell mediated immune response, indicating that it can induce various epitope specific immune responses. Based on that, the inventors investigated if B cells transduced with entire antigen by viral vector could induce immune response effectively. First, the present inventors prepared the adenovirus (AdHM) delivering a gene encoding the extracellular domain and the transmembrane domain of tumor-associated antigen Her-2/neu (HM) and then injected into a mouse model.

Particularly, B cells were separated from the splenocytes of BALB/c mice and then cultured for transduction with 100 MOI of the adenovirus introducing HM (AdHM, Viromed) in serum-free condition at 37° C. for 90 minutes. Then, a serum was supplemented thereto, followed by further culture for 8 hours, for 24 hours and for 48 hours respectively. The cells were stained with PE labeled anti-Her-2/neu antibody (BD biosciences #340552) for flow cytometry. The level of Her-2/neu expressed on the surface of cell was measured (the efficiency of adenovirus transduction for B cells and the percentage of PE+ cells in total B cells were investigated).

After 8 hours, 24 hours and 48 hours culture of B cells with adenovirus, it was confirmed that transduction efficiency was more than 20% under every culture condition (FIG. 20). Particularly, When B cells were co-cultured with AdHM for more than 8 hours, B cells were completely transduced with ADHM and thus Her-2/neu was expressed on the surfaces of the B cells. The expression of Her-2/neu on the B cell surface was not affected by culture with αGalCer. In addition, the ability of B cell to present αGalCer was not affected, either (FIG. 21). As explained hereinbefore, the above results indicate that when αGalCer is presented to DN32.D3 cells by CDld molecule on B cell, the activated DN32.D3 cells secret IL-2. Thus, measuring the level of IL-2 in the culture supernatant can confirm whether B cells are able to present αGalCer, and in the present invention, IL-2 secretion in the culture supernatant was confirmed, supporting that B cells can present αGalCer.

Example 9

Cytotoxic T Cell Response Induced by Adenovirus-Transduced B Cells

B cells were isolated from the splenocytes of BALB/c mice, which were transduced with 100 M.O.I. of the adenovirus expressing Her-2/neu extracellular domain and the transmembrane domain in serum-free condition in a 37° C. incubator for 60 minutes. Then, a serum was supplemented thereto, followed by further culture for 24 hours to prepare B/AdHM cells. AdHM-transduced B cells were cultured in a serum containing medium supplemented with 1-2 μg/ml of αGalCer for 23 hours, resulting in αGalCer-loaded B cells (B/AdHM/αGalCer). The prepared B cells were washed with RPMI more than three times to eliminate remained adenovirus and αGalCer.

The present inventors administered the B cell vaccine intravenously to mice to investigate whether B cells transduced with the AdHM could induce cytotoxic immune response. B cells alone (B) and αGalCer-loaded B cells (B/αGalCer) administered mice were used as a negative control. Her-2/neu specific cytotoxic T cell responses induced by AdHM-transduced B cells (B/AdHM) and αGalCer and AdHM co-pulsed B cells (B/AdHM/αGalCer) were measured. After immunization, target cells loaded with cytotoxic T cell epitope peptide (Her-2/neu$_{63-71}$, Anygene) were injected, followed by investigation of in vivo CTL activity.

As a result, after one week after the immunization, target cell lysis was not observed in the group immunized with B alone and B/αGalCer, while cytotoxic T cell response was observed in the mouse group immunized with B/AdHM and B/AdHM/αGalCer (FIG. 22). Adenovirus-transduced B cell activation can effectively induce in vivo cytotoxic T cell response without the aid of natural killer T cells, indicating that they can be used as antigen-presenting cells. The cytotoxic T cell response induced by B/AdHM and B/AdHM/αGalCer was reduced gradually, but up to 7 weeks from the immunization, the response continued to the significant level (FIG. 23). One week after the immunization, secretion of IFN-γ in CD8+ T cells was measured along with cytotoxic T cell response. As a result, the number of activated CD8+ T cells was increased in the mouse group treated with B/AdHM and B/AdHM/αGalCer, compared with that in the group treated with B cells only, and more specifically the number of CD8+ T cells in the group treated with B/AdHM/αGalCer was a little higher than that in the group treated with B/AdHM (FIG. 24).

Example 10

Activation of Natural Killer Cells by αGalCer-Loaded B Cells and Improvement of Vaccine Effect of Adenovirus-Transduced B Cell Vaccine <10-1> Activation of Natural Killer Cells by αGalCer-Loaded B Cells The activated natural killer cells were calculated based on those secreting IFN-γ. Specifically, B cells were isolated from the splenocytes of mice and then cultured in a medium containing 1 μg/ml of GolgiPlug for 5 hours. The cells were stained with anti-mouse IFN-γ:APC, CD3:PE, and CD49b:FITC antibody (all Biolegend). Natural killer cells were composed of those expressing CD49b, a natural killer cell marker, but not CD3.

The cytotoxic T cell response in the group treated with adenovirus and αGalCer co-pulsed B cells (B/AdHM/αGalCer) was higher and continued longer than that in the group treated with adenovirus-transduced B cells (B/AdHM), but the difference was not significant. These results indicate that the loading of αGalCer does not enhance the cytotoxic T cell response, unlike the peptide-pulsed B cell-based vaccine. But, the administration of the αGalCer-loaded B cell-based vaccine stimulated natural killer T cells in vivo, unlike the adenovirus-transduced B cell-based vaccine, and thereby activated natural killer cells (FIG. 25). Antitumor effect can be expected by activating natural killer cells and thereby inducing cytotoxic T cell response.

<10-2> Improvement of Vaccine Effect of the αGalcer and Adenovirus Co-Loaded B Cell-Based Vaccine To investigate the efficiency of inducing cytotoxic T cell response of the B cell vaccine, the present inventors administered the cell vaccine by a suboptimal dose that is not enough to induce complete cytotoxic T cell response and then measured the target cell lysis. A positive control group was treated with B cells loaded with αGalCer and cytotoxic T cell epitope peptide (B/αGalCer/pep). One week after the immunization with each B cell vaccine, the efficiency of inducing cytotoxic T cell response was compared between the groups treated respectively with B/AdHM and B/AdHM/αGalCer (FIG. 26). In the group administered with B/αGalCer/pep, most of B cells were considered to present an antigen, but only 20% of the total B cells transduced with adenovirus could be worked as antigen-presenting cells. Therefore, it is judged that the B cell vaccine transduced with adenovirus to introduce the whole antigen can induce the antigen-specific cytotoxic T cell response efficiently even though dosage is higher than that of the peptide-pulsed B cell vaccine. Besides, when the small amount of B cells (short of effective dose) was administered, it also could induce the target cell lysis with the aid of natural killer T cells activated by the loaded αGalCer.

Example 11

Adenovirus-Transduced B Cell Vaccine Inducing Antigen-Specific Antibody Response The adenovirus-transduced B cell-based vaccine has an advantage of simultaneously inducing humoral immune response and cell-mediated immune response, unlike the peptide-pulsed B cell vaccine inducing cell-mediated immune response only. To confirm whether the AdHM-transduced B cell vaccine could induce Her-2/neu specific antibody, BALB/c mice were immunized with B/AdHM and B/AdHM/αGalCer respectively. To measure anti-Her-2/neu antibody titer in serum, the binding of antibody to TAUF cells, murine tumor cells expressing Her-2/neu on the surface, was investigated by flow cytometry.

To measure the antibody response, blood samples were prepared on the $1^{st}$, $3^{rd}$, $5^{th}$ and $7^{th}$ week from the immunization by eye bleeding. The mouse blood samples stood at room temperature for 2 hours, followed by centrifugation at 8,000 for 10 minutes to separate serum. To measure anti-Her-2/neu antibody titer in the serum, the serum was diluted serially every two-fold from 1:50 (with PBS containing 1% FBS, 0.09% azide), followed by culture with TAUF, tumor cells expressing Her-2/neu, at 4° C. for 60 minutes. The TAUF cells incubated with mouse serum were washed with a buffer, followed by staining of the mouse antibody binding to TAUF cells by using FITC-labeled goat anti-mouse IgG antibody as a secondary antibody. Then, the amount of mouse antibody bound to TAUF was measured by flow cytometer (FACSCaliber, BD Biosciences), and the antibody titer was calculated by standardizing naive mouse serum and considering mean fluorescence intensity increased more than 1.8 fold as a positive response.

As a result, consistent with the result of inducing cytotoxic T cells, anti-Her-2/neu antibody titers in the groups immunized with B/AdHM and B/AdHM/αGalCer were maintained as high (FIG. 27) and humoral immune response was also induced in the above two groups, unlike in the groups treated with B cells and B/αGalCer (FIG. 28).

Example 12

Prophylactic and Therapeutic Effect on Cancer by the Immunization with the αGalCer-Loaded Adenovirus-Transduced B Cell-Based Vaccine $2\times10^5$ cells of TAUF were injected into the tail vein of BALB/c mice, a Her-2/neu tumor model, to induce a tumor. Then, the tumor bearing mice were immunized with B cell vaccines, followed by investigation of the survival rate.

The present inventors examined whether the adenovirus-transduced B cell vaccine could induce cell-mediated immune response and humoral immune response together and thereby has an antitumor activity. TAUF cells were intravenously injected into mice to induce lung cancer, in which the prophylactic and therapeutic effect of the B cell vaccine was measured. B cell vaccine was administered for immunization at the concentration of $2\times10^6$, and 7 days later $2\times10^5$ tumor cells were intravenously injected into the mouse, followed by investigating the survival rate. The survival period was extended in the groups treated with αGalCer-loaded B cells (B/αGalCer) and adenovirus-transduced B cells expressing tumor antigen (B/AdHM), compared with that in the group treated with B cells only (B). When mice were immunized with the αGalCer-loaded adenovirus-transduced B cell vaccine expressing a tumor antigen (B/AdHM/αGalCer), the mouse survived all through the experiment. These results indicate that B/AdHM/αGalCer vaccine has better antitumor effect than B/αGalCer or B/AdHM vaccine (FIG. 29, up). And it was judged that the immune response induced by the B cell vaccine can prevent tumor growth effectively.

Next, to confirm the therapeutic effect of the B cell vaccine, $5\times10^4$ tumor cells (TAUF) were injected into the tail vein to induce lung cancer. Three days later, the groups of mice were immunized with $1\times10^6$ B cells, B/αGalCer, B/AdHM and B/AdHM/αGalCer respectively. The shortest survival time was observed in the group treated with B cells only, and the survival time of B/αGalCer group was similar. In the meantime, the survival time of the group immunized with B/AdHM vaccine was somewhat extended, compared with those of groups treated with B cells only and B/αGalCer. On the contrary, the survival time was significantly extended in the group immunized with B/AdHM/αGalCer, which was consistent with the result of prophylactic models, indicating that B/AdHM/αGalCer vaccine has better antitumor effect than B cells, B/αGalCer or B/AdHM vaccine (FIG. 29, down).

Formulative Example

Preparation of Injectable Solution

The injectable solution of the antitumor vaccine of the present invention was prepared as follows.

1-2 μg/ml of αGalCer, $5\times10^6$ cells/ml of B cells, 1-2 μg/ml of a peptide, 1 g of 5'-chloro-3,2'-dihydroxychalcone or 5'-chloro-2,3'-dihydroxychalcone hydrochloride, 0.6 g of NaCl and 0.1 g of ascorbic acid were dissolved in distilled water, resulting in 100 ml solution for injection. The solution was poured in a bottle, which was sterilized at 120° C. for 30 minutes.

INDUSTRIAL APPLICABILITY

As explained hereinbefore, B cells of the present invention which are loaded with the natural killer T cell ligand, in particular αGalCer, and an antigen not only induce cytotoxic T lymphocyte response to the similar level as the conventional DC vaccine does but also have prophylactic and therapeutic effect on solid tumor and metastatic tumor. B cells transduced with adenovirus encoding a tumor antigen can induce the antigen specific immune responses, so that a vaccine mediated by the B cells can be used as a prophylactic and therapeutic agent for tumor. In addition, the vaccine of the invention can induce immune response even without the aid of CD4+ T cells. Therefore, it can be effectively administered to a HIV infected patient who has immune deficiency caused by the lack of CD4+ T cells.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. An immunotherapeutic vaccine comprising a pharmaceutically acceptable carrier and a composition selected from the group consisting of: ligand and antigen co-pulsed B-cells; and ligand-loaded antigen expressing B cells; wherein the ligand is a natural killer T cell ligand.

2. The immunotherapeutic vaccine according to claim 1, wherein the natural killer T cell ligand is selected from the group consisting of α-galacturonosylceramide, α-glucuronosylceramide, phosphatidylinositoltetramannoside, isoglobotrihexosylceramide, ganglioside GD3, phosphatidylcholine, β-galactosylceramide, lipophosphoglycan, glycoinositol phospholipid, αGalCer derivatives, β-anomeric galactosylceramide, α-anomeric galactosylceramide, bacteria lipid antigen, and αGalCer variants.

3. The immunotherapeutic vaccine according to claim 1, wherein the antigen originated either from pathogens including pathogenic bacteria, virus and parasite or tumor antigen.

4. The immunotherapeutic vaccine according to claim 3, wherein the pathogenic bacteria derived antigen is selected from a group consisting of *Bordetella pertussis* antigen (pertussis toxin, filamentous hemagglutinin and pertactin), tetanus toxoid, diphtheria antigen (diphtheria toxoid), *Helicobacter pylori* antigen (capsula polysaccharides of serogrup A, B, C, Y and W-135), pneumococcal antigen (*Streptococcus pneumoniae* type 3 capsular polysaccharide), tuberculosis antigen, cholera antigen (cholera toxin B subunit), staphylococcal antigen (staphylococcal enterotoxin B), *shigella* antigen (*shigella* polysaccharides), *Borrelia* sp, antigen, *Candida albicans* antigen and Plasmodium antigen.

5. The immunotherapeutic vaccine according to claim 3, wherein the virus derived antigen is selected from a group consisting of influenza virus antigen (hemagglutinin and neuraminidase antigen), human papilloma virus (HPV) antigen (glycoprotein), vesicular stomatitis virus antigen (vesicular stomatitis virus glycoprotein), cytomegalovirus (CMV) antigen, hepatitis virus antigen (hepatitis A(HAV), B(HBV), C(HCV), D(HDV) and G(HGV) antigen) (core antigen and surface antigen), respiratory syncytial virus (RSV) antigen, herpes simplex virus (HSV) antigen, human immunodeficiency virus (HIV) antigen (GP-120, GP-160, p18, Tat, Gag, Pol and Env) and the combinations thereof.

6. The immunotherapeutic vaccine according to claim 3, wherein the tumor antigen is selected from a group consisting of HPV E6/E7, gp100, tyrosinase, TRP-1 (tyrosinase-related protein-1), TRP-2 (tyrosinase-related protein-2), MAGE, MUC-1, CEA (carcinoembryonic antigen), p53, alpha-fetoprotein and Her-2/neu.

7. The immunotherapeutic vaccine according to claim 1, wherein the antigen is in the form of peptide, lipopolysaccharide, polysaccharide, glycoprotein or polynucleotide.

8. The immunotherapeutic vaccine according to claim 1, wherein the antigen is expressed by transduction with a recombinant virus.

9. The immunotherapeutic vaccine according to claim 8, wherein the recombinant virus is selected from a group consisting of adenovirus, adeno-associated virus, retrovirus, vaccinia virus, poxvirus and Sindbis virus to introduce a gene encoding an antigen.

10. An isolated natural killer T cell activator comprising αGalCer-loaded antigen-expressing B cells as an effective ingredient and a pharmaceutically acceptable carrier.

11. An isolated cytotoxic response inducer comprising αGalCer-loaded tumor antigen-expressing B cells as an effective ingredient.

12. An isolated natural killer T cell activator comprising αGalCer-loaded antigen-pulsed B cells as an effective ingredient and a pharmaceutically acceptable carrier.

* * * * *